United States Patent [19]
Guan et al.

[11] Patent Number: 5,643,758
[45] Date of Patent: Jul. 1, 1997

[54] PRODUCTION AND PURIFICATION OF A PROTEIN FUSED TO A BINDING PROTEIN

[75] Inventors: Chudi Guan, Wenham, Mass.; Hiroshi Inouye, deceased,, late of Philadelphia; Frank N. Chang, administrator, Dresher, both of Pa.

[73] Assignees: New England Biolabs, Inc., Beverly, Mass.; Temple University, Philadelphia, Pa.

[21] Appl. No.: 374,145

[22] Filed: Jan. 12, 1995

Related U.S. Application Data

[63] Continuation of Ser. No. 19,981, Feb. 17, 1993, which is a continuation of Ser. No. 737,596, Jul. 25, 1991, abandoned, which is a continuation of Ser. No. 196,988, May 20, 1988, abandoned, which is a continuation-in-part of Ser. No. 24,053, Mar. 10, 1987, abandoned.

[51] Int. Cl.$^6$ .......................... C12P 21/00; C12N 15/70
[52] U.S. Cl. .......................... 435/69.7; 435/320.1
[58] Field of Search .................. 435/69.1, 69.7, 435/172.3, 320.1; 536/23.1, 23.4; 935/23

[56] References Cited

FOREIGN PATENT DOCUMENTS

WO84/03103  8/1984  WIPO .

OTHER PUBLICATIONS

Rasmussen et al. (1984) J. Bacteriol. 160:612–617.
Ito et al. (1981) Cell 24:707–717.
Nagai et al. (1984) Nature 309:810–812.
Duplay et al. (1984) J. Bio. Chem. 259:10606–10613.
Bassford et al. (1979) 139:19–31.

*Primary Examiner*—David Guzo
*Assistant Examiner*—Robert Schwartzman
*Attorney, Agent, or Firm*—Gregory D. Williams; Peter F. Corless

[57] ABSTRACT

Methods and products are provided for producing and/or purifying virtually any hybrid polypeptide molecule employing recombinant DNA techniques. More specifically, a DNA fragment coding for a protein molecule, e.g. a polypeptide or portion thereof, is fused to a DNA fragment coding for a binding protein, such as the gene coding for the maltose binding protein. The fused DNA is inserted into a cloning vector and an appropriate host transformed. Upon expression, a hybrid polypeptide is produced which can be purified by contacting the hybrid polypeptide with a ligand or substrate to which the binding protein has specific affinity, e.g. by affinity chromatography. The hybrid polypeptide so purified may in certain instances be useful in its hybrid form, or it may be cleaved to obtain the protein molecule itself by, for example, linking the DNA fragments coding for the target and binding proteins with a DNA segment which codes for a peptide which is recognized and cut by a proteolytic enzyme, such as Factor Xa. The present invention also relates to certain vectors useful in practicing the above process.

24 Claims, 11 Drawing Sheets

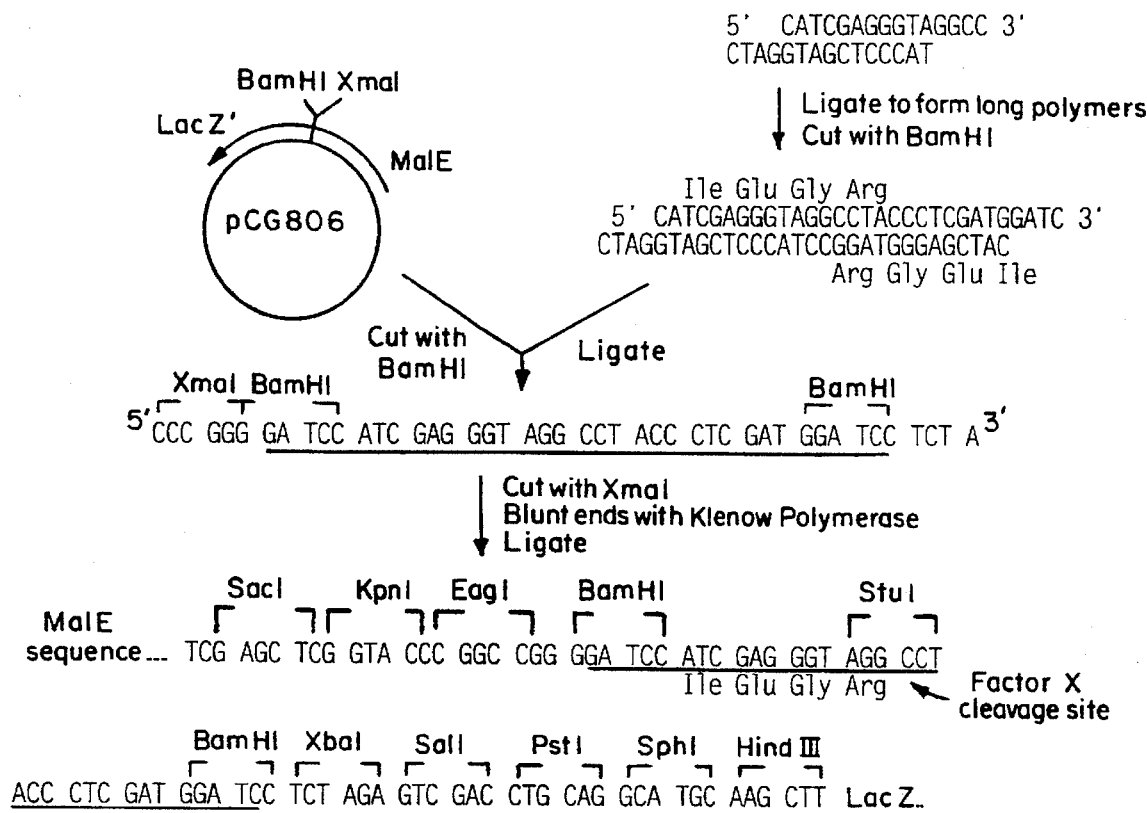
FIG. 12A
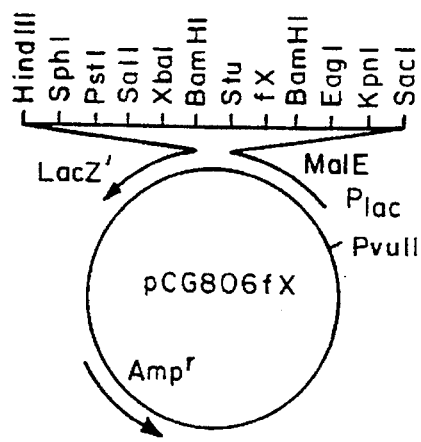
FIG. 12B
FIG. 12C

PRODUCTION AND PURIFICATION OF A PROTEIN FUSED TO A BINDING PROTEIN

This is a continuation of application Ser. No. 08/019,981, filed on Feb. 17, 1993, which is a continuation of application Ser. No. 07/737,596, filed Jul. 25, 1991, now abandoned, which is a continuation of application Ser. No. 07/196,988, filed on May 20, 1988, now abandoned, which is a continuation-in-part of U.S. Ser. No. 024,053 filed on Mar. 10, 1987, abandoned.

BACKGROUND OF THE INVENTION

The present invention relates to a process of producing and/or purifying virtually any hybrid polypeptide or fused protein molecule employing recombinant DNA techniques. More specifically, a DNA fragment coding for a protein molecule, e.g. a polypeptide or portion thereof, is fused to a DNA fragment coding for a binding protein such as the gene coding for the maltose binding protein. The fused DNA is inserted into a cloning vector and an appropriate host transformed. Upon expression, a hybrid polypeptide or fused protein molecule is produced which can be purified by contacting the hybrid polypeptide with a ligand or substrate to which the binding protein has specific affinity, e.g. by affinity chromatography. The hybrid polypeptide so purified may in certain instances be useful in its hybrid form, or it may be cleaved to obtain the protein molecule itself by, for example, linking the DNA fragments coding for the protein molecule and binding protein with a DNA segment which codes for a peptide which is recognized and cut by a proteolytic enzyme. The present invention also relates to certain vectors useful in practing the above process as well as to a bioreactor and methods employing the bound hybrid polypeptide, e.g. where the bound fused polypeptide is contacted and reacted with a susbstrate which interacts with the bound protein molecule to produce a desired result.

Recently developed techniques have made it possible to employ microorganisms, capable of rapid and abundant growth, for the synthesis of commercially useful proteins and peptides. These techniques make it possible to genetically endow a suitable microorganism with the ability to synthesize a protein or peptide normally made by another organism. In brief, DNA fragments coding for the protein are ligated into a cloning vector such as a plasmid. An appropriate host is transformed with the cloning vector and the transformed host is identified, isolated and cultivated to promote expression of the desired protein. Proteins so produced are then isolated from the culture medium for purification.

Many purification techniques have been employed to harvest the proteins produced by recombinant DNA techniques. Such techniques generally include segregation of the desired protein based on its distinguishing molecular properties, e.g. by dialysis, density-gradient centrifugation and liquid column chromatography. Such techniques are not universally applicable and often result in consumption of the purification materials which may have considerably more value than the protein being purified, particularly where substantial quantities of highly purified protein are desired.

Other procedures have been developed to purify proteins based on solubility characteristics of the protein. For example, isoelectric precipitation has been employed to purify proteins since the solubility of proteins varies as a function of pH. Similarly, solvent fractionatton of proteins is a technique whereby the solubility of a protein varies as a function of the dielectric constant of the medium. Solvent fractionation, while giving good yields often causes denaturation of the protein molecule. Neither isoelectrtc precipitation nor solvent fractionation are useful in obtaining highly purified protein. Such techniques are typically employed in tandem with other procedures.

Proteins have also been separated based on their ionic properties by e.g. electrophorests, ion-exchange chromatography, etc. Such electrophoretic techniques, however, have been used as analytical tools and are not practical as a means for purifying proteins on a large scale. Moreover, high purity and yield of the protein obtainable by such techniques is rarely achieved in a single step.

Affinity chromatography has also been employed in the purification of biopolymers such as proteins. Affinity chromatography involves a selective adsorbent which is placed in contact with a solution containing several kinds of substances including the desired species to be purified. For example, when used in protein purification protocols, affinity chromatography generally involves the use of a ligand which specifically binds to the protein to be purified. In general, the ligand is coupled or attached to a support or matrix and the coupled ligand contacted with a solution containing the impure protein. The non-binding species are removed by washing and the desired protein recovered by eluting with a specific desorbing agent. While affinity chromatography produces a relatively high level of purified protein, this technique requires significant amounts of the protein-specific ligand employed for purification. Moreover, the ligand will be different for each and every protein to be purified which necessarily entails a time-consuming and laborious regime. In addition, it has been found that specific ligands do not exist for all types of protein molecules, such as certain enzymes. As a result, affinity chromatography has not been successfully employed as a universal isolation purification technique for protein molecules.

One proposed attempt to universalire affinity chromatography to all proteins is described in European Patent Application 0,150,126 (Hopp). Disclosed is the preparation of a hybrid molecule produced by recombinant DNA techniques employing gene fusion. One gene codes for the desired protein to be purified while the other codes for an identification or marker peptide. The marker peptide contains a highly antigenic N-terminal portion to which antibodies are made and a linking portion to connect the marker peptide to the protein to be purified. The linking portion of the marker peptide is cleavable at a specific amino acid residue adjacent the protein molecule to be purified by use of a specific proteolytic agent. The fused or hybrid protein is isolated by constructing an affinity column with immobilized antibody specific to the antigenic portion of the marker peptide. The antibody binds to the fused protein which can thereafter be liberated from the column by a desorbing agent. The marker peptide may then be cleaved from the desired protein molecule with a proteolytic agent.

While purportedly overcoming some of the problems described above for protein purification protocols, Hopp requires substantial amounts of antibodies specific for the antigenic portion of the marker peptide. Moreover, the quantity of desorbing agent (in this case, a small peptide) required to compete off the target protein is substantial as well as a significant cost factor. Also, the desorbing agent must be purified away from the target protein. Thus, scale up for this system would not be practical. Furthermore, regeneration of the chromatographic column may be extremely difficult due to the destabilizing conditions employed to wash out the column after use, which may, in fact destroy the column. Others have suggested the use of low affinity antibody columns. However, low affinity columns often result in non-specific binding and would require significant cost for any large scale purification.

Thus, there is a continuing need for techniques which enable large scale purification of proteins produced through recombinant DNA processes without the above described problems. It would be particularly advantageous to provide an affinity purification process which utilizes an abundant and inexpensive ligand to which the fused protein would bind and an equally abundant and inexpensive desorbing agent.

SUMMARY OF THE INVENTION

In accordance with the present invention there is provided a method for producing and highly purifying virtually any protein molecule generated by recombinant DNA techniques in a single affinity chromatography step. More specifically, a hybrid polypspride or fused protein is produced by recombinant DNA techniques, the hybrid polypeptide comprising a protein molecule and a binding protein. The hybrid polypeptide can be isolated and purified directly, e.g. from the crude cellular extract or culture medium, simply by contacting the extract containing the hybrid polypeptide with a substrate to which the binding protein has specific affinity, e.g. using affinity chromatography. The bound hybrid polypeptide can easily be liberated from the column in a highly purified form with a desorbing agent which slectively desorbs the bound binding protein. While the target protein may be useful in its hybrid form, in certain preferred embodiments, it may be desirable to separate or cleave the binding protein away from the target protein. This may be accomplished in a variety of ways. For example, a DNA fragment coding for a predetermined peptide, e.g. a linking sequence, may be employed to link the DNA fragments coding for the binding and target proteins. The predetermined peptide is preferably one which is recognized and cleaved by a proteolytic agent such that it cuts the hybrid polypeptide at or near the target protein without interfering with the biological activity of the target protein. The linking sequence, in addition to providing a conventene proteolytic cleavage site, may also serve as a polyltnker, i.e. by providing multiple DNA restriction sites to facilitate fusion of the DNA fragments coding for the target and binding proteins, and/or as a spacer which separates the target and binding protein which, for example, allows access by the proteolytic agent to cleave the fused polypeptide.

The preferred affinity column useful in practicing the present invention, in general, comprises a column containing immobilized ligand or substrate to which the binding protein has a specific affinity. As will be appreciated by the skilled artisan, the specific affinity of a binding protein for a given substrate will depend both on the particular binding protein employed as well as the substrate used in the column. In general, the substrate used in the column should bind substantially all of the particular binding protein without binding other proteins to which it is exposed. In certain instances, however, depending on the particular application (e.g. whether the column is used to purify the protein molecule or as a bioreactor for reacting the protein molecule with a substance with which it interacts to produce a desired result), a substrate may be used which only binds a portion of the binding protein present. In addition, the particular substrate employed should permit selective desorbtion of the bound binding protein with a suitable desorbing agent.

It will be appreciated that the column thus prepared can be used to isolate and purify virtually any protein which, by recombinant DNA techniques is linked to the binding protein to form a hybrid polypeptide. The hybrid polypeptide can be released from the column with a suitable desorbing agent and/or cleaved with a proteolytic agent to separate the target protein from the binding protein. Alternatively, in accordance with another embodiment of the present invention, the bound hybrid polypepttde may be used as a bioreactor for reacting, for example, the biologically active portion of the protein molecule (which may be an enzyme, restriction endonuclease, etc.) with a substrate which interacts with the target protein. For example, if the target protein is an enzyme, the affinity column can serve as a means for immobilizing that enzyme, i.e. by the binding protein portion of the hybrid polypspride being bound to the column. The substrate upon which the enzyme acts is thereafter passed through the column to achieve the desired result.

BRIEF DESCRIPTION OF THE DRAWINGS

FIG. 12A illustrates the construction of pCG806fx. FIG. 12B is the schematic diagram of pCG806fx. FIGS. 12C shows the nucleotide sequence of the joint region between malE and the paramyosin coding sequence.

DETAILED DESCRIPTION OF THE INVENTION

Figure 1:
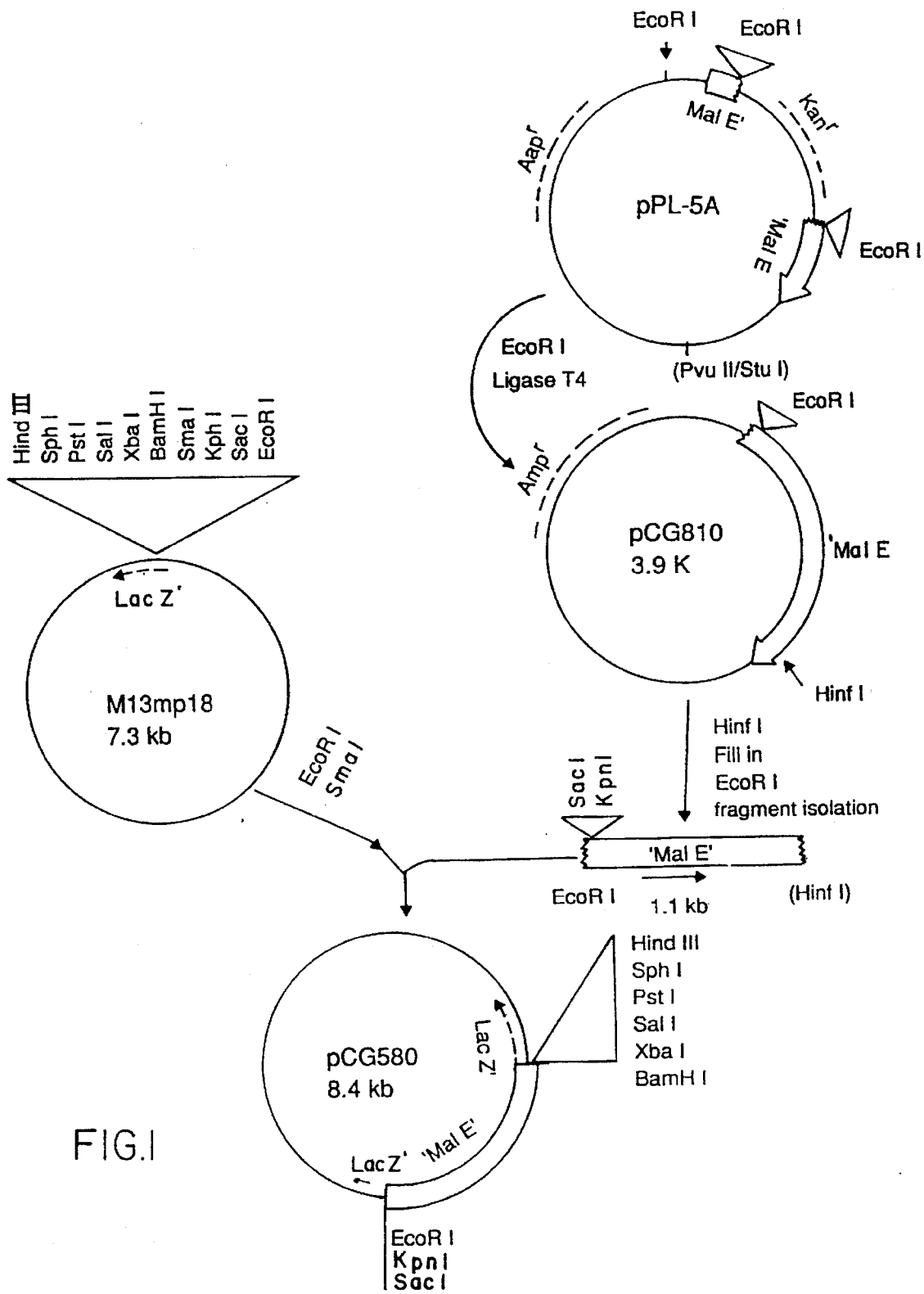
FIGS. 1 and 2 illustrate the construction of the maltose binding protein fusion cloning vector pCG150.

The present invention provides a novel approach for producing and purifying virtually any polypeptide or protein molecule obtained by recombinant DNA techniques. The protein molecule is produced by constructing a cloning vector containing fused genes comprising a gene encoding the protein molecule and a gene coding for a binding protein or portion thereof which has a specific affinity for a ligand or substrate and expressing the fusion in an appropriate host. The substrate is used as the matrix in an isolation/purification protocol, e.g. an affinity column, to recover the expressed product of the fused genes, i.e. the hybrid polypeptide. A DNA fragment which codes for a predetermined polypeptide can be used, e.g. flanking the gene coding for the binding protein, in order to adjust the reading frame for the desired gene fusion and/or to introduce into the hybrid poltpeptide a peptide sequence which is recognized and cleaved by a proteolytic agent which enables separation of the protein molecule from the binding protein where desired. As noted above, the bound hybrid polypeptide may also be used as a bioreactor for reacting the biologically active portion of the protein molecule with a substrate which interacts with the protein molecule.

The methods described herein by which DNA coding for a hybrid polypeptide is preferably cloned, expressed and purified include the following steps:

I. Preparation of Fusion Vector
  A) The DNA encoding for the desired binding protein is purified.
  B) The DNA is inserted into a cloning vector such as pBR322 and the mixture is used to transform an appropriate host such as E. coli.
  C) The transformants are selected, such as with antibiotic selection or other phenotypic selection.
  D) The plasmid DNA is prepared from the selected transformants.
  E) The binding activity domain of the protein is determined and convenient restriction endonuclease sites are identified by mapping or created by standard genetic engineering methods.

II. Insertion of DNA Coding for the Protein Molecule into the Fusion Vector
  A) The protein molecule gene is cloned by standard genetic engineering methods.
  B) The protein molecule gene is characterized, e.g. by restriction mapping.
  C) A DNA restriction fragment which encodes the protein molecule is prepared.
  D) The protein molecule DNA fragment is inserted in the binding protein fusion vector so that an in-frame protein fusion is formed between the the DNA fragment coding for the binding protein and the DNA fragment coding for the protein molecule.
  E) The vector containing this hybrid DNA molecule is introduced into an appropriate host.

III. Expression and Purification of the Hybrid Polypeptide
  A) The host cell containing the fusion vector is cultured.
  B) Expression of the fused gene is induced by conventional techniques.
  C) A cell extract containing the expressed fused polypeptide is prepared.
  D) The hybrid polypeptide is separated from other cell constitutants using an affinity column having as a matrix a substance to which the binding protein part of the hybrid polypeptide has a specific affinity.
  E) The bound purified hybrid polypeptide can be recovered and/or utilized by the following methods:
    (1) if the protein molecule's biological activity is maintained in its hybrid or fused configuration it may recovered from the column by eluting with a desorbing agent and used directly after elution in its hybrid form;
    (2) the protein molecule may be separated from the binding protein either before or after elution from the column by proteolytic or chemical cleavage; and
    (3) the column may be used as a bioreactor with the fusion protein immobilized on the column, e.g. by contacting and reacting the bound fusion protein with a substrate which interacts with the biologically active portion of the protein molecule.

Binding Protein

Binding proteins which may be employed in accordance with the present invention include the sugar (e.g. mono-, di- or polysaccharide) binding proteins such as maltose or arabthose binding protein, lectin binding proteins, vitamin binding proteins such as avidin, nucleic acid binding proteins, amino acid binding proteins, metal binding proteins, receptor proteins, sulfate binding proteins, phosphate binding proteins, and the like. Sugar and polysaccharide binding proteins are preferred. The preferred sugar binding protein for practicing the present invention is the maltose binding protein.

The product of the mal E Gene of E. coli, i.e. realrose binding protein (MBP) is a periplasmic osmotically shockable protein. MBP exhibits specific binding affinity with maltose and maltodextrins. Macromolecular alpha (1–4) linked glucans are also bound with high affinities. Ferenci, T. and Klotz, U. Escherichia Coli. FEBS Letters, Vol. 94, No. 2. pp. 213–217 (1978), the disclosure of which is hereby incorporated by reference. The dissociation constants are around 1 um. Kellermann et al., Coli Eur. J. Biochem. 47. 139–149 (1974), the disclosure of which is hereby incorporated by reference. MBP is usually considered to exist as a monomer although it can exist as a dimer. Maltose induces the conversion of the dimer to the monomer. Gilbert, Biochemical and Biophysical Research Communications (1982) Vol. 105, No. 2, pp. 476–481, the disclosure of which is hereby incorporated by reference. MBP is a secreted protein which is synthesized in cytoplasm as a precursor with a 26 amino acid N-terminal signal peptide. Dupley, et al. J. Biol. Chem. Vol. 259 pp. 10606–10613 (1984), the disclosure of which is hereby incorporated by reference. During translocation across the cytoplasmic membrane the signal peptide is removed and the mature MBP is released into the periplasmic space. Mature MPB contains 370 amino acids corresponding to a molecular weight of 40,661 dalton( Dupley, et al., supra). MBP is made in large quantity in an induced culture ($2-4 \times 10^4$ monomers per cell). It has been determined that MBP and at least four other proteins make up the maltose transport system of E. coli. Shuman, J. Biol. Chem. 257:5455–5461 (1982), the disclosure of which is hereby incorporated by reference. Besides being an essential component of the maltose transport system, MBP is also the specified chemoreceptor of the bacterium for maltose and maltodextrins. The Mal E gene has been cloned and sequenced. Dupley, et al., supra.

Linking Sequence

A DNA fragment coding for a predetermined peptide may be employed to link the DNA fragments coding for the binding protein and protein molecule. The predetermined peptide is preferably one which recognized and cleaved by a proteolytic agent such that it cuts the hybrid polypeptide at or near the protein molecule without interfering with the biological activity of the protein molecule. One such DNA fragment coding for a predetermined polypeptide is described in Nagai et al., Nature, Vol. 309., pp. 810–812 (1984), the disclosure of which is hereby incorporated by reference. This DNA fragment has the oligonucleotide sequence: ATCGAGGGTAGG and codes for the polypeptide Ile-Glu-Gly-Arg. This polypeptide is cleaved at the carboxy side of the argtntne residue using blood coagulation factor Xa. As noted above the linking sequence, in addition to providing a convenient cut site, may also serve as a polylinker, i.e. by providing multiple restriction sites to facilitate fusion of the DNA fragments coding for the target and binding proteins, and/or as a spacing means which separates the target and binding protein which, for example, allows access by the proteolytic agent to cleave the hybrid polypeptide.

Protein Molecule

The present invention may be beneficially employed to produce substantially any prokaryotic or eukaryotic, simple or conjugated protein that can be expressed by a vector in a transformed host cell. Such proteins include enzymes including endonucleases, methylases, oxidoreductases, transferases, hydrolases, lyases, isomerases or ligases.

The present invention also contemplates the production of storage proteins, such as ferritin or ovalbumin or transport proteins, such as hemoglobin, serum albumin or ceruloplasmin. Also included are the types of proteins that function in contractile and motile systems, for instance, actin and myosin.

The present invention also contemplates the production of antigens or antigenic determinants which can be used in the preparation of vaccines or diagnostic reagents.

The present invention also contemplates the production of proteins that serve a protective or defense function, such as the blood proteins thrombin and fibrinogen. Other protective proteins include the binding proteins, such as antibodies or immunoglobulins that bind to and thus neutralize antigens.

The protein produced by the present invention also may encompass various hormones such as Human Growth Hormone, somatostatin, prolactin, estrone, progesterone, melanocyte, thyrotropin, calcitonin, gonadotropin and insulin. Other such hormones include those that that have been identified as being involved in the immune system, such as interleukin 1, intereukin 2, colony stimulating factor, macrophage-activating factor and interferon.

The present invention is also applicable to the production of toxic proteins, such as rictn from castor bean or grossypin from cotton linseed.

Proteins that serve as structural elements may also be produced by the present invention; such proteins include the fibrous proteins collagen, elastin and alpha-keratin. Other structural proteins include glyco-proteins, virus-proteins and muco-proteins.

In addition to the above-noted naturally occurtng proteins, the present invention may be employed to produce synthetic proteins defined generally as any sequences of amtno acids not occurring in nature.

Genes coding for the various types of protein molecules identified above may be obtained from a variety of prokaryotic or eukaryotic sources, such as plant or animal cells or bacteria cells. The genes can be isolated from the chromosome material of these cells or from plasmids of prokaryottc cells by employing standard, well-known techniques. A variety of naturally occuring and synthetic plasmids having genes encoding many different protein molecules are now commercially available froma variety of sources. The desired DNA also can be produced from mRNA by using the enzyme reverse transciptase. This enzyme permits the synthesis of DNA from an RNA template.

Preparation of DNA Fusion and Expression Vectors

Various procedures and materials for preparing recombinant vectors; transforming host cells with the vectors; replicating the vector and expressing polypsprides and proteins; are known by the skilled artisan and are discussed generally in Maniatis et al., Molecular Cloning: A Laboratory Manual, CSH 1982, the disclosure of which is hereby incorporated by reference.

In practicing the present invention, various cloning vectors may be utilized. Although the preferred vector is a plasmid, the skilled artisan will appreciate that the vector may be a phage. If cloning takes place in mammalian or plant cells, viruses can also be used as vectors. If a plasmid is employed, it may be obtained from a natural source or artificially synthesized. The particular plasmid chosen should be compatible with the particular cells serving as the host, whether a bacteria such as E. coli, yeast, or other unicellular microorganism. The plasmid should also have the proper origin of replication (replicon) for the particular host cell chosen. In addition, the capacity of the vector must be sufficient to accommodate the fusion coding for both the protein molecule of interest and the binding protein.

Another requirement for a plasmid cloning vector is the existence of restriction enzymes to cleave the plasmid for subsequent ligation with the foreign genes without causing inactivation of the replicon while providing suitable ligatable termini that are complementary to the termini of the foreign genes being inserted. To this end, it would be helpful for the plasmid to have single substrate sites for a large number of restriction endonucteases.

Moreover, the plasmid should have a phenotypic property that will enable the transformed host cells to be readily identified and separated from cell is which do not undergo transformation. Such phenotypic selection genes can include genes providing resistance to a growth inhibiting substance, such as an antibiotic. Plasmids are now widely available that include genes resistant to various antibiotics, such as tetracycline, streptomycin, sulfa drugs, and ampicillin. When host cells are grown in a medium containing one of these antibiotics, only transformants having the appropriate resistant gene will survive.

Figure 2:
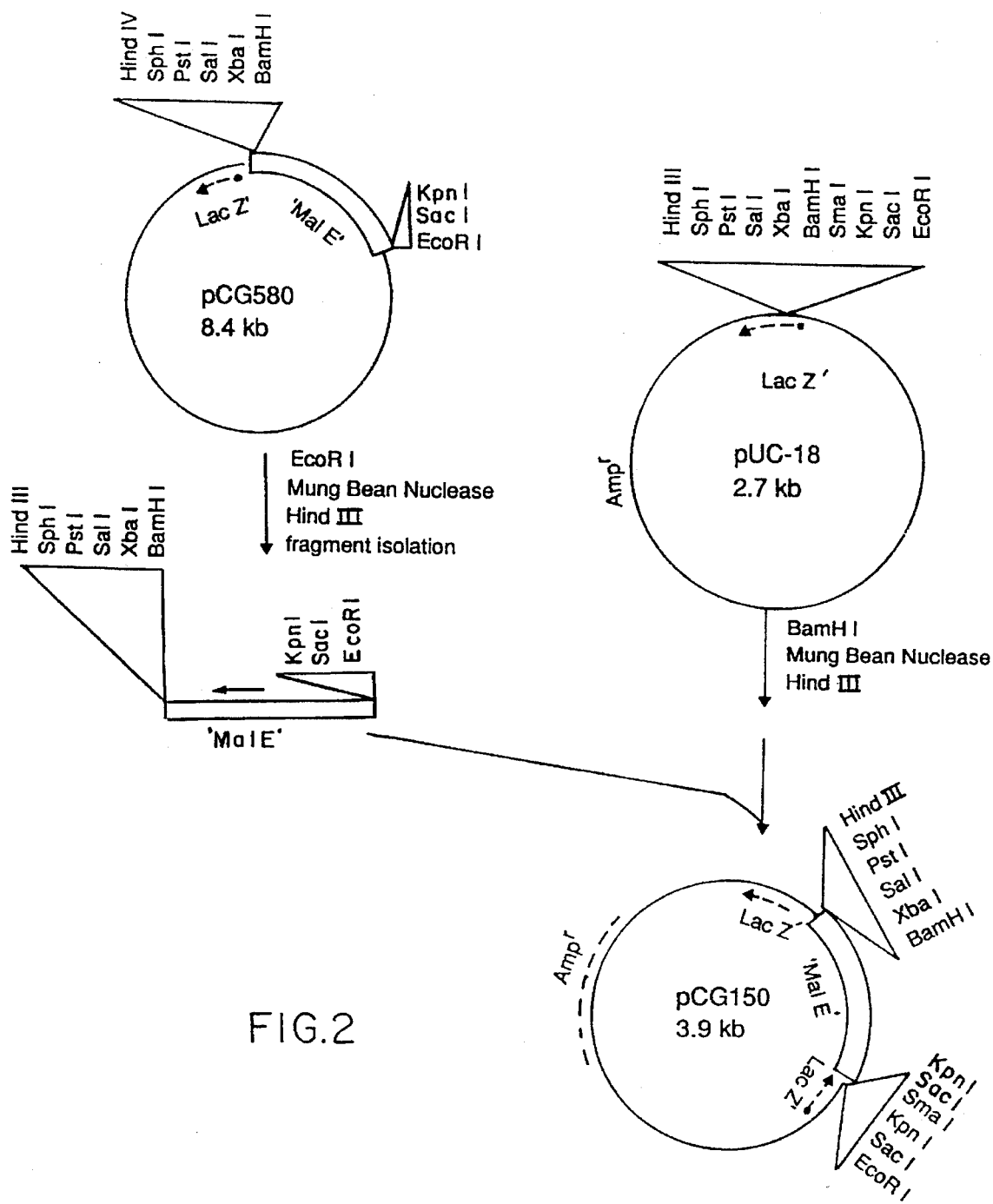

If E. coli is employed as the host cell, a preferred plasmid for performing the present invention is pCG150. A partial restriction endonuclease cleavage map of this plasmid is shown in FIG. 2. An alternative plasmid for high level expression in E coli is pCG806.

To prepare the chosen plasmid for ligation, preferably, it is digested with a restriction endonuclease to produce a linear segment(s) in which the two DNA strands are cleaved at closely adjacent sites to produce cohesive termtnt ("sticky ends") bearing 5'-phosphate- and 3'-hydroxyl groups, thereby facilitating ligation with the foreign genes. For the plasmids identified above, restriction endonucleases will produce this result.

Certain restriction enzymes (Pvu II, Bal I) may result in the formation of blunt ends. The blunt ends of the plasmid can be joined to the foreign genes with T4 DNA ligase. The methods and materials for achieving efficient cleavage and ligation are well known in the art.

Prior to being joined with the selected cloning vector, it is desirable that the foreign genes coding for the binding protein and the protein molecule be first joined together. Ideally, the gene coding for the protein molecule molecule is treated with the same restriction endonuclease used to cleave the plasmid vector so that the appropriate termini of the gene will be compatible with the corresponding termini of the plasmid. This gene also may be treated with a second, different restriction endonuclease to prepare its opposite terminus for ligation with the binding protein gene.

The cointegrate genes are next ligated to the linearized plasmid fragment in a solution with DNA ligase. After incubation, the recircularized plasmid having the correct orientation of the cointegrate genes are identified by standard techniques, such as by gel electrophoresis.

Transformation of Recombinant DNA Plasmid

The recombinant DNA plasmids, as prepared above, are used for the transformation of host cells. Although the host cell may be any appropriate prokaryotic or eukaryotic cell, preferably it is well-defined bacteria, such as E. coli or yeast strain. Both such hosts are readily transformed and capable of rapid growth in fermentation cultures. In place of E. coli, other unicellular microrganisms can be employed, for instance fungae and algae. In addition, other forms of bacteria such as salmonella or pneumococcus may be substituted for *E. coli*. Whatever host is chosen, it should be one that has the necessary biochemical pathways for phenotypic expression and other functions for proper expression of the hybrid polypeptide. The techniques for transforming recombinant plasmids in *E. coli* strains are widely known. A typical protocol is set forth in Maniatus et al. supra.

In transformation protocols, only a small portion of the host cells are actually transformed, due to limited plasmid uptake by the cells. Thus, before transformants are isolated, the host cells used in the transformation protocol typically are multiplied in an appropriate medium. The cells that actually have been transformed can be identified by placing the original culture on agar plates containing a suitable growth medium containing the phenotypic identifier, such as an antibiotic. Only those cells that have the proper resistance gene will survive. Cells from the colonies that survive can be lysed and then the plasmid isolated from the lysate. The plasmid thus isolated can be characterized, e.g. by digestion with restriction endonucleases and subsequent gel electrophorests or by other standard methods.

Once transformed cells are identified, they can be multiplied by established techniques, such as by fermentation. In addition, the recovered cloned recombinant plasmids can be used to transform other strains of bacteria or other types of host cells for large scale replication and expression of the fused protein.

Purification of the Fused Protein

The hybrid polypeptide expressed by the transformed host cell are preferably separated from all other cellular constitutents and growth media by an affinity chromatography process. The column matrix is simply any substrate for which the binding protein has specific affinity. For example, when the binding protein is MBP the column matrix may be crosslinked amylose. Crosslinked amylose prepared by an epichlorohydrin protocol satisfies the substrate specificity of MBP and provides a rapid one step chromatographic purification of MBP from osmotic-shock fluids, Ferenci, T. et al., supra, whole cell extracts or culture media.

An extract from the transformed host cell is contacted with the column to isolate the hybrid polypeptide. The hybrid polypepetide may thereafter be eluted from the column, for example, by adding a dilute solution of a desorbing agent which displaces the hybrid polypeptide.

Separation of the Protein Molecule from the Hybrid Polypeptide

The hybrid polypeptide purified from the above affinity column may be cleaved by sequence specific proteases such as a factor Xa or by discrete chemical cleavage such as cyanogen bromide.

The following examples are given to additionally illustrate embodiments of the present invention as it is preferred to practice. It should be understood that these examples are illustrative, and that the invention is not to be considered as restricted thereto except as indicated in the appended claims.

EXAMPLE I

Example I describes cloning, expression and purification of B-galactosidase as a product of the mal E—Lac Z gene fusion.

Preparation of the Binding Protein Fusion Vector

Plasmid pPL-5A is the source for the Mal E encoding DNA fragment which is prepared by first creating a deletion derivative of pPL-5A which moves the Mal E promoter and signal sequence. This plasmid is pCG810. The gene encoding Mal E is then resected from pCG810 and inserted into M13mp18 to produce recombinant phage pCG580, which has added multiple cloning sites to facilitate insertion of protein molecule encoding DNA. The Male E gene now carrying the additional cloning site is resected from pCG580 and inserted into pUC18 in order to create additional cloning sites as well as pick up a selective antibiotic resistance gene. The resulting plasmid is the protein fusion vector pCG150 which contains the Mal E gene and additional cloning sites and which is used in the construction of the vector which also contains the DNA coding for the desired protein molecule, infra. A sample of pCG150 has been deposited with the American Type Culture Collection, 12301 Parklawn Drive, Rockville, Md. 20852 on Mar. 10, 1987 under ATCC accession No. 67345. The construction of plasmid pCG150 is illustrated in FIGS. 1 and 2.

According to the published Mal E gene sequence of *E. coli* there are five Taq I recognition sites in the gene. One is located at base number 83–86 (Dupley, et al. supra) corresponding to the second and third codon of mature maltose binding protein (MBP) coding sequence. A kanamycin resistance determinant fragment flanked by polylinkers was inserted into this Taq I site. The resulting plasmid was pPL-5A.

5–10 ug of pPL-5A plasmid DNA and 10units of EcoRI restriction enzyme in 100 ul of EcoRI digestion buffer was incubated for 2 hours at 37° C. 20 ul of DNA gel loading buffer (0.25% bromophenol blue, 40 mM EDTA, pH 8.0, 30% glycerol) were added and mixed. The digested sample was applied to 1% low gelling temperature agarose gel (Seaplaque). Gel electrophoresis was performed at low current (20 mA) for 4 hours. TEA gel electrophoresis buffer (40 mM Tris-acetate, pH 8.0. 2 mM EDTA) was used. The gel was stained with TEA buffer containing ethidium bromide 0.5 ug/ml for 30 minutes at room temperature. Three DNA bands were visualized on the gel by U.V. irradiation. The largest fragment was cut out of the gel and placed in a 1.5 ml microfuge tube. The tube was incubated for 5 minutes in a 65° C. water bath. The melted gel (about 100 ul) was extracted wtth an equal volume of phenol and phenol/chloroform and chloroform as described by Mantatis et al, supra, at page 170, the disclosure of which is hereby incorporated by referernce. The aqueous phase was saved and ¹⁄₁₀ volume of 3N sodium-acetate pH 5.5 was added and mixed. 2.5 volumes of ethanol was added. The ethanol precipitate mixture was placed in −70° C. freezer for 20 minutes (or in −20° C. freezer overnight), then centrifuged for 15 minute in a mtcrofuge at 4° C. The supernatant was discarded and the pellet was rinsed with 0.5 ml of 70% ethanol twice. The tube was left open at room temperature to eliminate any remaining ethanol. The DNA pellet was dissolved in 19 ul of water followed by adding 4 ul of 6× ligation buffer (300 mm Tris-HCl pH 7.4, 60 mm Mg $Cl_2$, 60 mm dithigthreitol, 6 mM ATP, 600 ug BSA) and 1 ul of T4 DNA ligase (10 units) and incubated at 16° C. overnight. The ligation solution was used to transform competent cells of *E. coli* strain SF 1362. The competent cells were made and the transformation was performed as described by T. J. Silhavy et al., in Experiments with Gene Fusions, CSH pp. 169–170 (1984), the disclosure of which is hereby incorporated by reference. After heat shock the transformation mixture was incubated. with 5 ml LB medium for 45 minutes at 37° C. The cells were collected by centrifugation for 5 minutes at 3000 r.p.m. and resuspended in 0.5 ml of LB medium. 0.05–0.2 ml of the cells were spread on LB plates containing ampicillin 100 ug/ml. After overnight incubation at 37° C. a total of about 1000 transformants were obtained. 16 transformants were purified on the same plates. Plasmid DNA minipreparations from the purified transformants were performed as described by Silhavy et al., supra. Restriction enzyme analysis on the plasmid DNAs was also performed. One plasmid was chosen, pCG810, in which the kanamycin resistance determenent sequence and the male promotor and signal sequence regions had been deleted and the single EcoR,I BglII, BssHII and NcoI cutting sites remained.

10–20 ug of plasmid pCG810 DNA prepared and purified by the BND cellulose procedure described by Gamper et al., DNA, Vol. 4, No.2 (1985), the disclosure of which is hereby incorporated by reference, and 20 units of Hinf I restriction enzyme in 100 ul of Hinf I digestion buffer (recommended by N.E.B.) were incubated for 2 hours at 37° C. then extracted with phenol and chloroform and precipitated with ethanol as described above. The DNA was dissolved in 50 ul of the filling in reaction buffer (50 mm Tris. pH 7.4. 10mM $MgCl_2$, 1 mM dithiothreitol, 0.1 mm dATP, 0.1 mM dCTP, 0.1 mM dGTP and 0.1 mM dTTP containing 5 units of DNA polymerase I large fragment and incubated for 20 minutes at room temperature. 50 ul of TE buffer (10 mM Tris. pH 8.0, 1 mm EDTA were added and extracted with phenol and chloroform and the aqueous phase precipitated with ethanol. The DNA was cleaved with EcoRI restriction enzyme in 100 ul of EcoRI digestion buffer followed by ethanol precipitation. The DNA was redissolved in 50 ul of TE followed by 10 ul of DNA gel loading buffer and applied to 1% of low gelling temperature agarose gel. The gel electrophoresis and DNA extraction from gel were as described above. The 1.1 kb EcoRI-Hinf I fragment which contained almost the entire MBP coding sequence was purified and dissolved in 10 ul of DNA buffer (10 mm Tris pH 8.0, 0.1 mM EDTA), stored at –20° C.

5 ug of M13mp18 double stranded DNA (Yantsch-Perron et al., Gene: 33, pp.103–119 at 104, (1985)), the disclosure of which is hereby incorporated by reference, and 10 Units of SmaI restriction enzyme in 50 ul of SmaI digestion buffer were incubated for 30 minutes at 37° C. followed by phenol extraction and ethanol precipitation as described above. The digested DNA was then dissolved in 50 ul of EcoRI digestion buffer containing 10 units EcoRI restriction enzyme and incubated for 1 hour, then extracted with phenol and chloroform, precipitated with ethanol as described above. The DNA pellet was dissolved in 10 ul of DNA buffer.

Two DNA preparations, the 1.1 kb EcoRI-HinfI fragment and the EcoRI and SmaI digested M13mp18 vector, were pooled and ligation was performed as described above. The ligation solution was used to transform JM101 or 71-18 competent cells (Yantsch-Peron et al., supra). The transformation was done as described above. After the heat shock the cells were mixed with JM101 or 71-18 exponentially growing cells and melted soft agar keeped at 47° C. and plated on LB plates containing XG and IPTG described by J. Messing in NIH Publication No. 79∝99, Vol. 2, (1979) at 43–48, the disclosure of which is hereby incorporated by reference. About 500 to 1000 plaques appeared on the plate; 60% were white, 40% blue. About 100 white plaques were picked up with sterile pasteur pipets and added to 5 ml culture tubes containing 2 ml early log phase culture of JM101 or 71-18. The tubes were incubated for 5–6 hours at 37° C. with shaking. The phage containing supernatants were seperated from the cells by transfering 1 ml each of culture into a microfuge tube and centrifugation for 10 minutes with microlugs at room temperature. 20 ul of supernatant were withdrawn and mixed with 1 ul of 2% S.D.S. and 4 ul of DNA gel loading buffer. Samples were electrcphoresed through 0.8% agarose gel in 4xTAE buffer overnight. The recombinant phages were identified by slower migration through the gel as compared with single stranded DNA of phage M13mp18. Double stranded DNAs were made from the recombinant phages and restriction enzyme analyses were carried out. One recombinant phage pCG580 was chosen which had the Mal E gene sequence insertion in the same direction as Lac Z gene on M13mp18, in which the EcoRI cutting site was regenerated. The BamHI-XbaI-SalI-PstI-SphI-BindIII polylinker remained. BglII, BssHII and NcoI cutting sites were introduced in by the insertion of the male sequence.

5 ug of pCG580 double stranded DNA purified with BND cellulose was cleaved with EcoRI restriction enzyme followed by blunting the cohesive ends with DNA polymerase I large fragment as described above. The DNA was religated and used to transform JM101 or 71-18. Only less than 5% of transformants were blue. It seemed that the filling in EcoRI cutting site created an in-frame TAA codon which could not be suppressed by Sup E carried by JM101. The small portion of blue transformants could be explained by a base deletion from the cohesive ends during the DNA manipulation and indicated the inserted Mal E sequence was in the same reading frame with down stream Lac Z sequence since no detectable DNA deletion was found for the plasmids made from the blue transformants by restriction enzyme analyses.

10–20 ug of double stranded pCG580 DNA purified with BND cellulose was cleaved with EcoRI. After phenol extraction and ethanol precipitation the DNA pellet was dissolved in 100 ul of mung bean exonuclease buffer containing about 5 units mung bean exonuclease and incubated for 20 minutes at 37° C. followed by phenol extraction and ethanol precipitation. The blunted DNA was then cleaved with Hind III restriction enzyme in 50 ul of Mind III digestion buffer. This sample was electrophoresed through 1% of low gelling temperature agarose gel. The 1.1 kb DNA fragment containing MBP coding sequence tailed with polylinker was purified from the gel as described above. The purified DNA fragment was stored in 10 ul of DNA buffer at –20° C.

10 ug of pUC-18 plasmid DNA and 20 units of BamHI restriction enzyme in 100 ul of BamHI digestion buffer were incubated for 1–2 hours at 37° C. After phenol extraction and ethanol precipitation the digested DNA was treated with mung bean exonuclease to blunt the cohesive ends as described above. After phenol extraction and ethanol precipitation the DNA was dissolved in 10 ul of DNA buffer.

Two DNA preparations, the 1.1 kb fragment from pCG580 and the BamHI cleaved pUC-18, were pooled and 4 ul of 6× ligation buffer and 1 ul of $T_4$ ligase (5–10 units) were added and mixed. The ligase solution was incubated overnight at 16° C. followed by incubation for 4 hours at room temperature and used to transform JM103 or 71-18. Transformants were selected on LB plates containing ampicillin 100 ug/ml. Recombinant plasmids were identified by the size of DNA with the toothpick assay as described by Shinmick et al., Nucl. Acids Res. Vol. 2, p. 1911, the disclosure of which is hereby incorporated by reference. About 12 recombinant plasmids were scored and three produced blue color on LB ampicillin plates in the presence XG and IPTG. One was chosen as plasmid pCG150. 5 ug of pCG150 plasmid DNA purified with BND cellulose was cleaved with EcoRI restriction enzyme followed by blunting the cohesive ends with large fragment DNA polymerase I, then ligated with $T_4$ Ligase. When this DNA was used to transform JM101 or 71-18, more that 95% of transformants were white in presence of XG and IPTG. This indicated no translation restatted in the downstream Mal E gene region.

Figure 3:
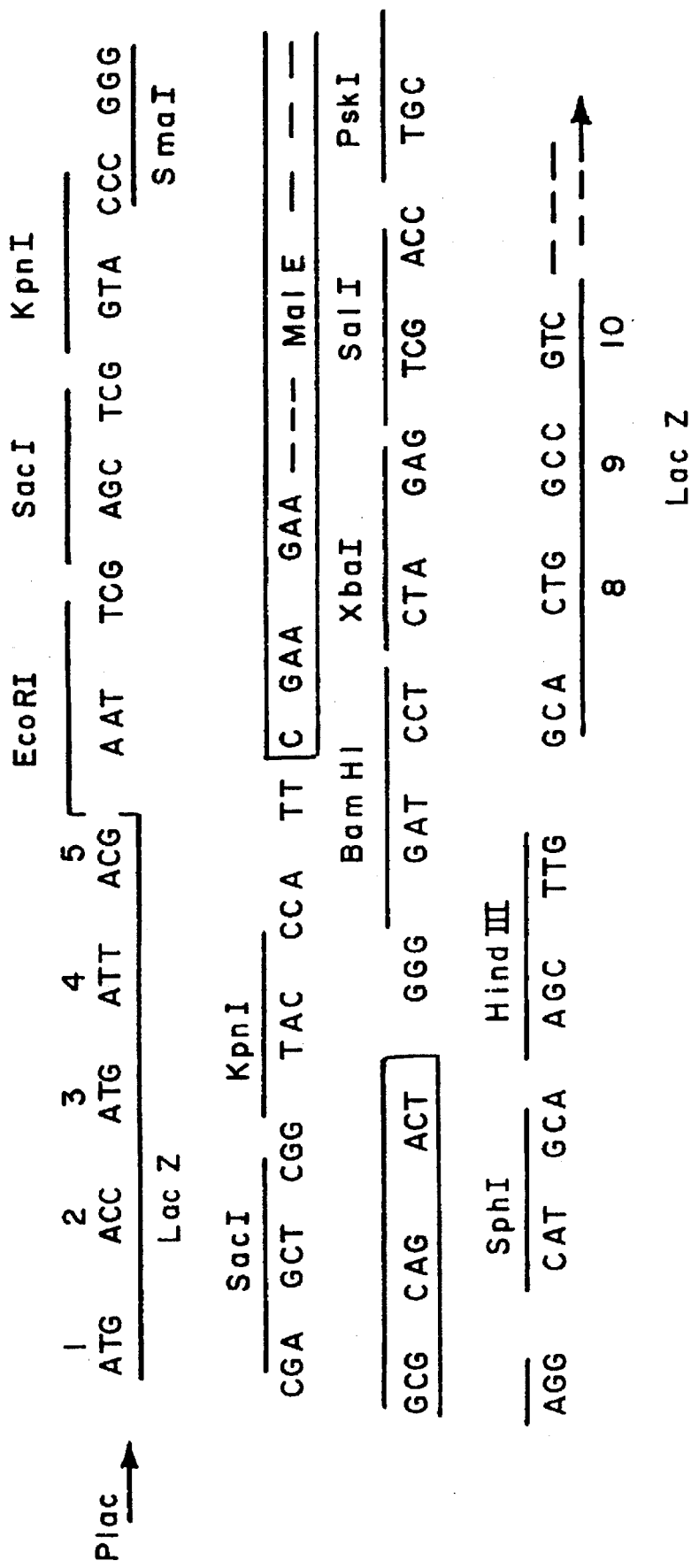
FIG. 3 illustrates the DNA sequence of the polylinker region of the cloning vector pCG150.

The Mal E gene joint regions on plasmid pCG150 were sequenced and the results presented in FIG. 3.

Figure 4:
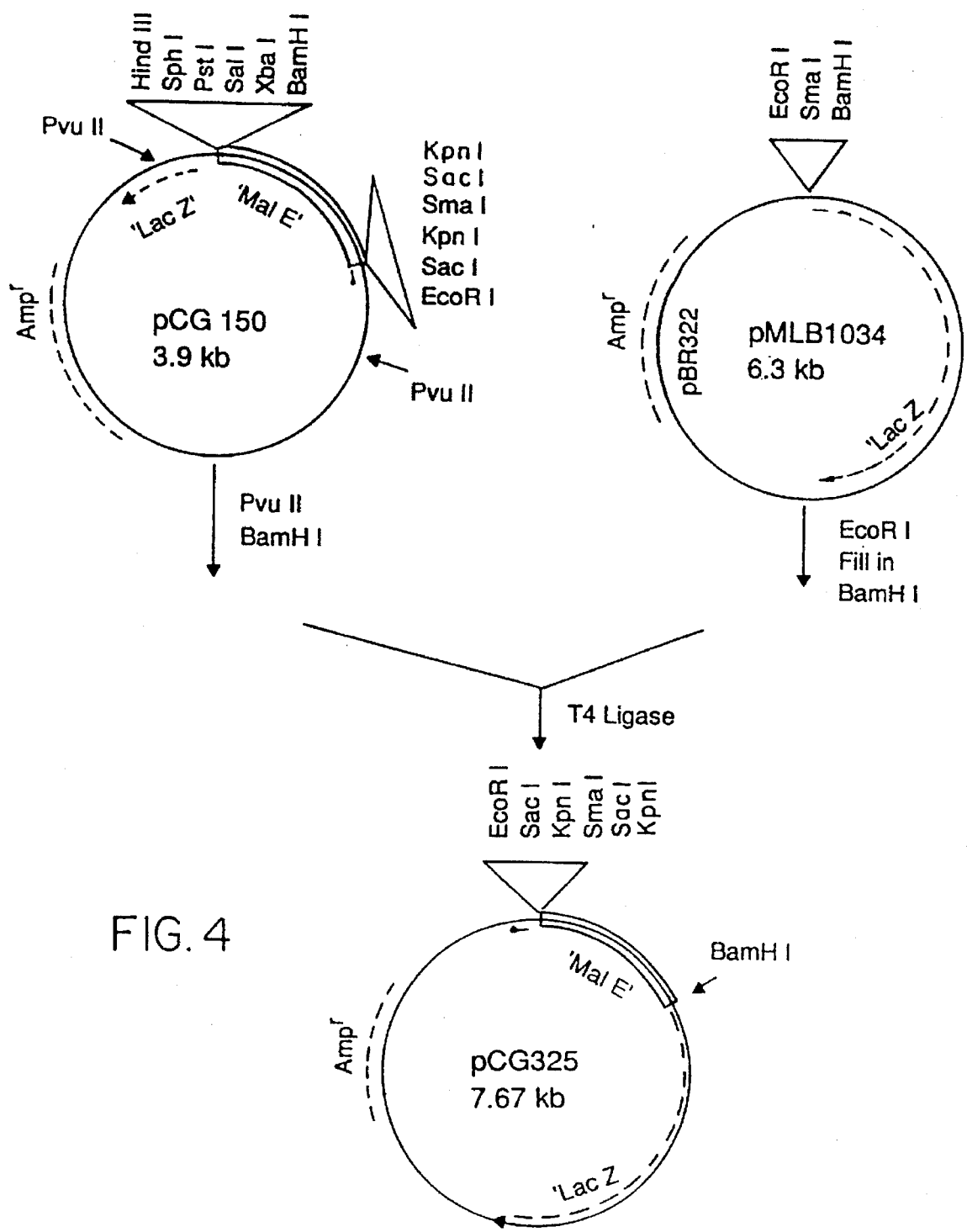
FIG. 4 illustrates the consruction of the mal E—Lac Z gene fusion plasmid pCG325.

The Mal E—B-galactosidase fusion protein plasmid pCG325 illustrated in FIG. 4 was constructed as follows. Plasmid pMLB1034 was constructed by Silhavy et al, supra. This plasmid contains the Lac Z gene coding for B-galactostdase without the promotor or first 8 codons of the protein and a polylinker containing EcoRI, SmaI and BamHI restriction sites. 5 ug of pMLB1034 was cleaved with EcoRI restriction enzyme followed by blunting the cohesive ends with DNA polymerase large fragment, then cleaved with BamHl. After phenol extraction and ethanol precipitation the DNA was dissolved in 10 ul of DNA buffer and stored at −20° C.

5 ug of pCG150 DNA was cleaved with BamHI and PVUII restriction enzymes, extracted with phenol chloroform, precipitated with ethanol. The DNA was dissolved in 10 ul of DNA buffer. Two pCG150 and PMLB1034 DNA preparations were pooled and ligated as described above. The ligation solution was used to transform competent cells made from an E. coli straim MC4100 Silhavy, T. J., et al, supra and spread on LB plates containing ampictllin 100 ug/ml, XG 20 ug/ml. After overnight incubation several hundred transformants appeared on plates, 20–30% of them were blue. About 24 blue transformants were purified and used to isolate plasmid DNAs usingh the rapid isolation method described by Silhavy, supra. Restriction enzyme analyses were performed on these plasmid DNAs.

One recombinant, plasmid pCG325, was chosen and characterized. This plasmid contained the 1.3 kb Mal E gene sequence from pCG150 which had been inserted in the EcoRI-BamHl site of pMLB1034.

Affinity Chromatography

A double deletion (_Lac_malB) strain E. coli (SF1362) habouring pCG325 was grown to late log phase in rich medium containing ampicillin 100 ug/ml. Cells were harvested by centrifugation with a Beckman centrifuge for 15 minutes at 5000 r.p.m. at 4° C. 5 gms of harvested cells were washed with 100 ml of 10 mM TRIS. pH 7.2 at 4° C., then resuspended in 50 ml of the same buffer. Cells were broken by sonication at 4° C. Cell debris was separated by centrifugation with a Beckman centrifuge for 30 minutes at 16000 r.p.m. The supernatant was dialysed against 1 L of the same buffer for 3–4 hours at 4° C. A sample was applied onto a 3×5 cm cross-linked amylose column prepared as described by Ferencz et al., supra at pp. 459–463.

Figure 5:
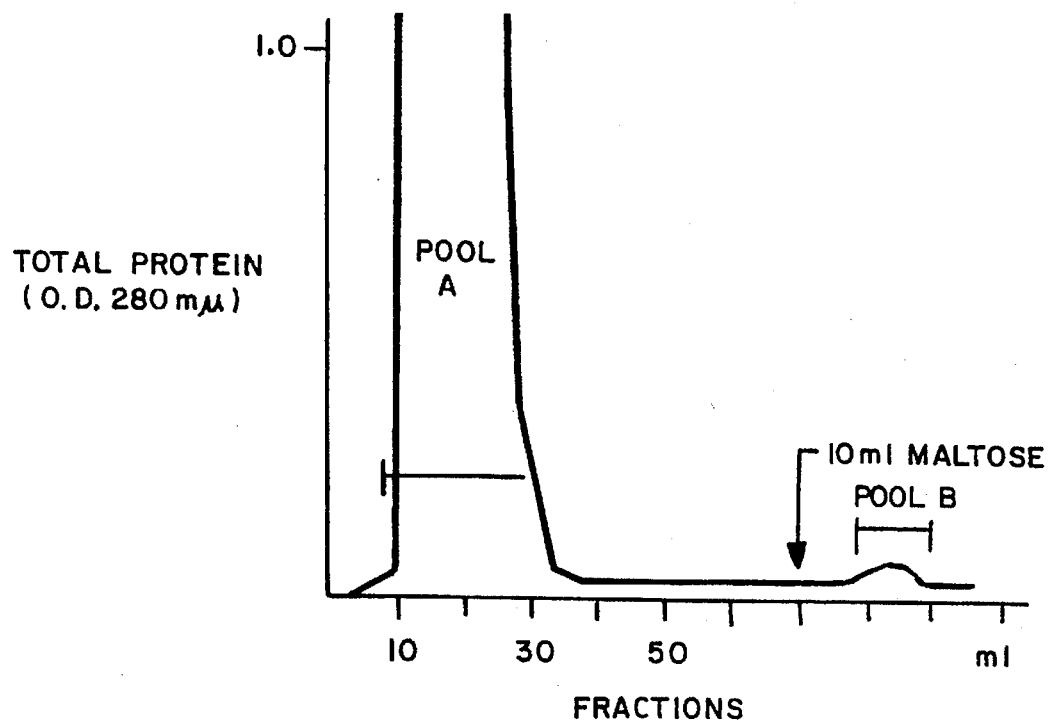
FIG. 5 illustrates elution profile of the protein resulting from affinity chromatography of a crude extract of SF1362/pCG325 containing the mal E—Lac Z fusion.
Figure 6:
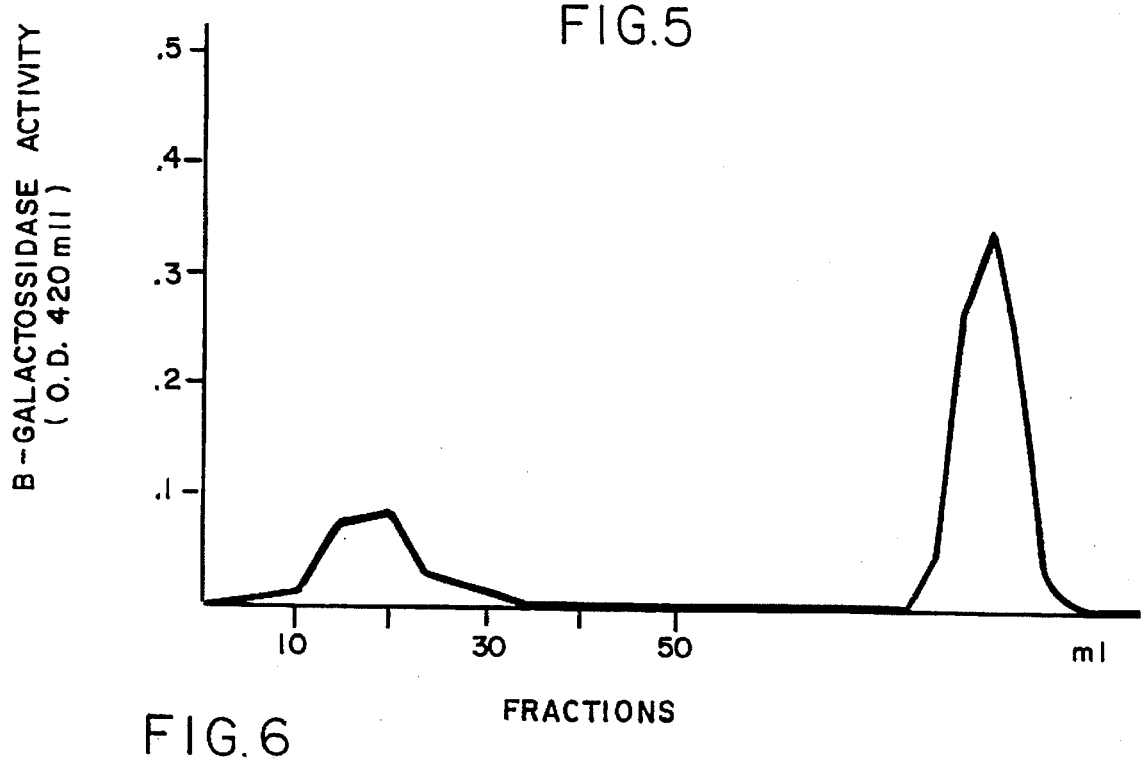
FIG. 6 illustrates the activity profile of the protein resulting from affinity chromatography of a crude extract of SF1362/pCG325 containing the mal E—Lac Z fusion.

After the major 280 mu absorbant peak passed through at about 20–30 ml the column was extensively washed with 10–20 column volume of 10 mM Tris pH 7.2. The column was eluted with 10 mM Tris, pH 7.2, containing 10 mM maltose. Both O.D 280 mu and B-galactosidase activity (Miller, Experiments in Molecular Genetics, CSH (1972), pp. 325–355, the disclosure of which is hereby incorporated by reference) were measured for each fraction. The eluting profiles are illustrated in FIG. 5. FIG. 6 shows that more than 95% of OD280 absorbing material in the crude extracts passed through the column. Only less then 1% was retained by the column and could be eluted with 10 mM maltose buffer. In contrast more than 70% of B-galactosidase activity was retained by the column and eluted with 10mM maltose (FIGS. 5 and 6). When the pass through fractions were pooled and reapplied onto another cross-linked amylose column, the B-galactostdase activity present in these fractions was not retained. This suggests that a small portion of the hybrid polypeptide was degraded to such a degree that the degraded products lost binding activity with cross-linked amylose, but still maintained some B-galactosidase enzymatic activity. When the maltose eluted fractions were dialysed and pooled and reapplied onto another cross-linked amylose column, the B-galactostdase activity present in these fractions was retained and could be eluted with 10 mM maltose buffer.

Polyacrylamide Gel Electrophoresis

Affinity chromatography peaks were pooled separately. The maltose eluted peak was concentrated 25–50 fold. 20–40 ul of concentrated sample were mixed with double strength loading buffer (0.5 M Tris-HCl, pH 6.8, 30% glycerol, 4% SDS, 6% beta-mercaptoethanol, 0.4% bromophenol blue) and boiled for two minutes. Samples were applied onto 7 or 10% polyacrylamide gel (29:1). The electrophorests buffer system was used as described by Laemmli, Nature, Vol. 227, pp. 680–685 (1970), the disclosure of which is hereby incorporated by reference. The gel electrophoresis was performed at 7–10 V/cm or 20 mA for 5 to 7 hours followed by staining with Coomasie Brillant blue R 250 (0.1% coomasie blue, 50% methanol, 10% acetic acid. The gels were desrained with desraining solution of 10% acetic acid and 10% methanol).

Figure 7:
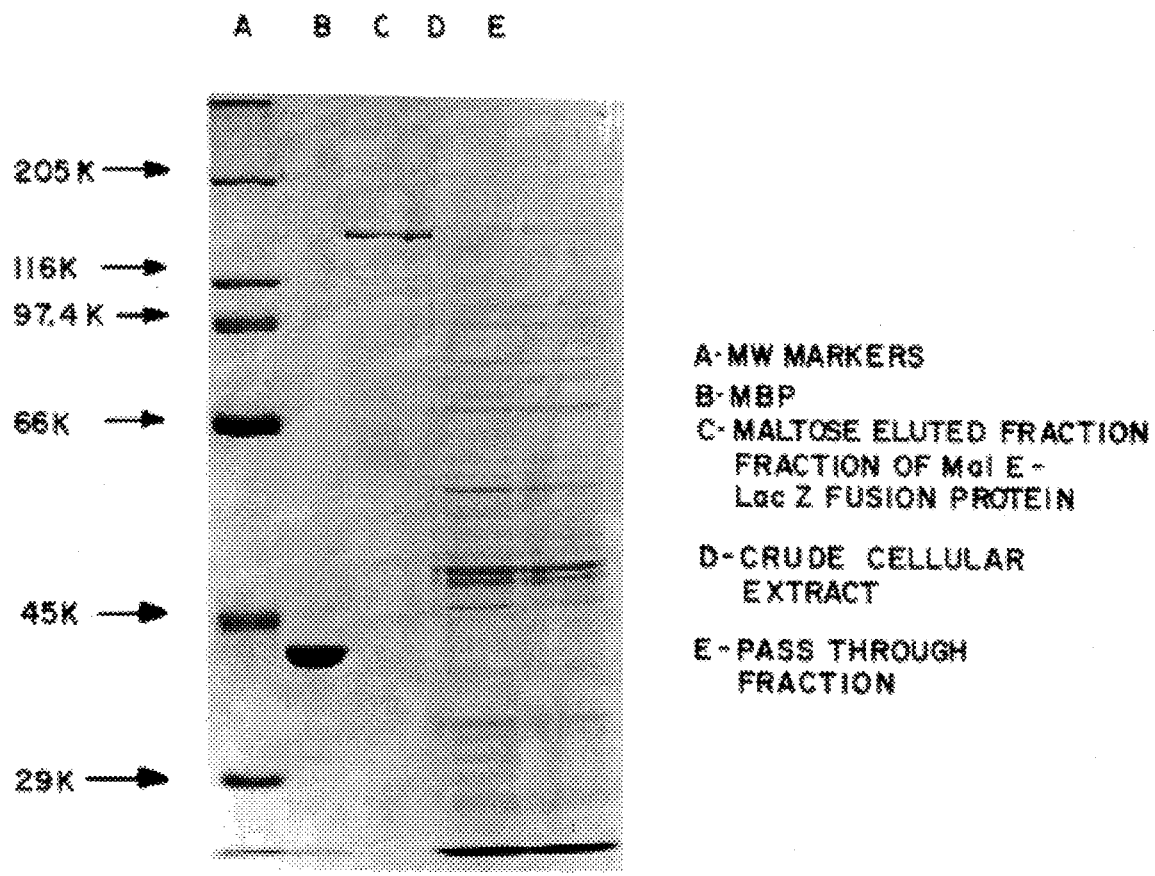
FIG. 7 illustrates the SDS polyacrylamide gel electrophoresis of the product of the mal E—Lac Z fusion.

The results of SDS gel electrophorests are shown in FIG. 7. It appeared that almost all of the protein in the crude extract passed through the column. Only the hybrid polypspride and small particles of its degraded products were retained by the column and eluted with maltose buffer. The math band on the gel represents the hybrid polypeptide whose molecular weight is estimated at 156 k, corresponding to that deduced from the gene fusion sequence.

Figure 8:
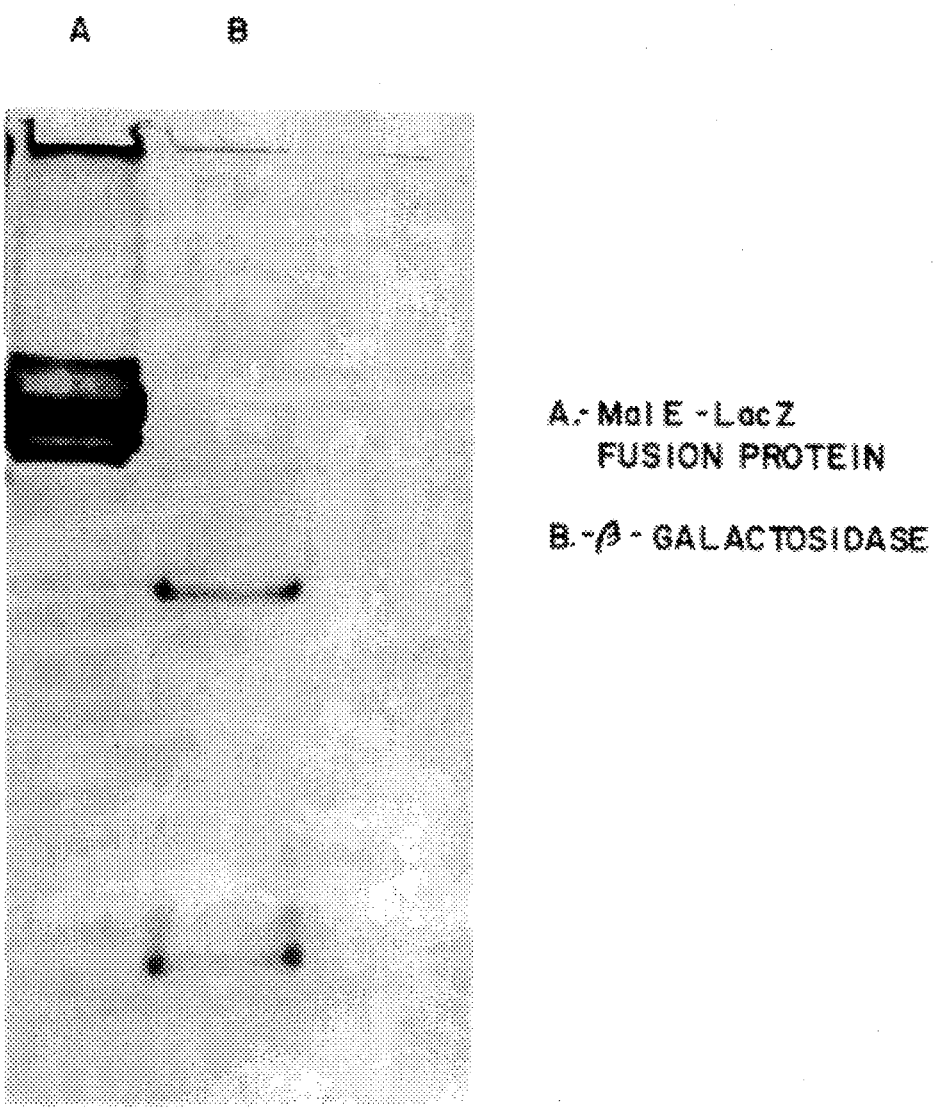
FIG. 8 illustrates the native polyacrylamide gel electrophorests of the product of the mal E—Lac Z fusion.

Native protein gel analysis was also carried out. For native gels the SDS was omitted from the electrophorests buffer system and the electrophorests gel was rinsed with water then covered with Z buffer 0.1M $NAPO_4$ pH 7.0, KCl 0.01M, $Mg2SO4$, 0.001M, B-Mercaptoethanol 0.05M) contaiing XG 20 ug/ml and incubated for 4 hours at 37° C. without shaking. When the blue band appeared on gel, the buffer was discarded. This shows that the hybrid polypspride, which migrated slower than the native B-galactosidese, represents the B-galactosidase enzymatic activity in the maltose buffer eluted fraction (FIG. 8).

Immunodiffusion Experiment

Double immunodiffusion (Ouchterlony) experiment was performed on 1% agarose gel in the buffer 10 mM Tris, pH 7.2 150 mM NaCl. 5–10 ug of sample protein were used (Anti MBP sara obtained from Jon Beckwith of Harvard Medical School. Anti B-galactostdase sara was obtained from Promega Biotech, Wis. The purified hybrid polypeptide formed precipitation lines with both anti MBP sera and anti B-galactosidase sera. Pure B-galactostdase formed a precipitation line only with anti B-galactosidase sera and the maltose binding proteins only with anti MBP sera.

EXAMPLE II

Example II describes the cloning, expression and purification of PstI restriction endonuclease as a product of the Mal E-Pst I restriction gene fusion.

Recombinant DNA

Figure 9:
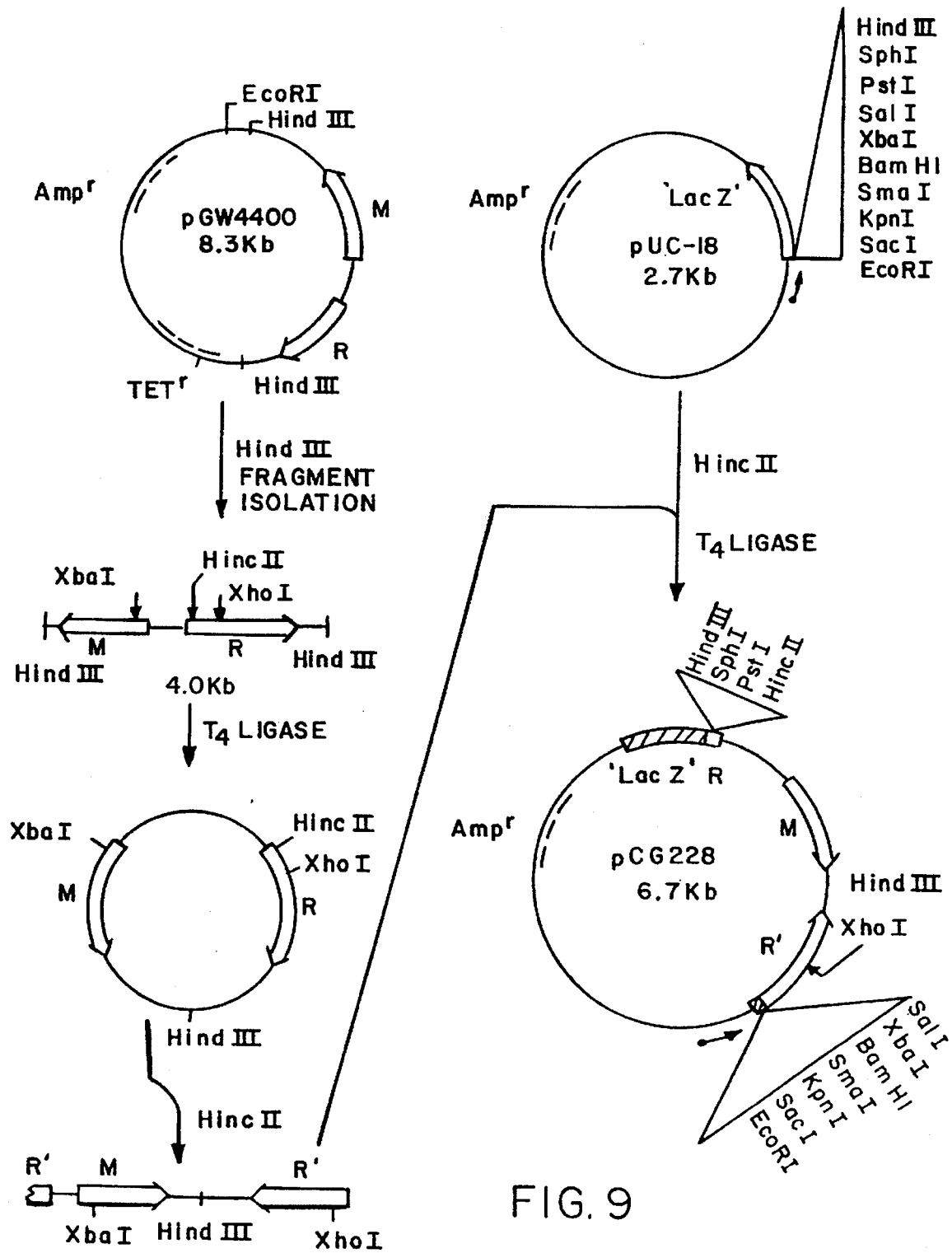
FIGS. 9 and 10 illustrate the construction of the mal E—Pst I restriction endonuclease gene fusion plasmid pCG410.
Figure 10:
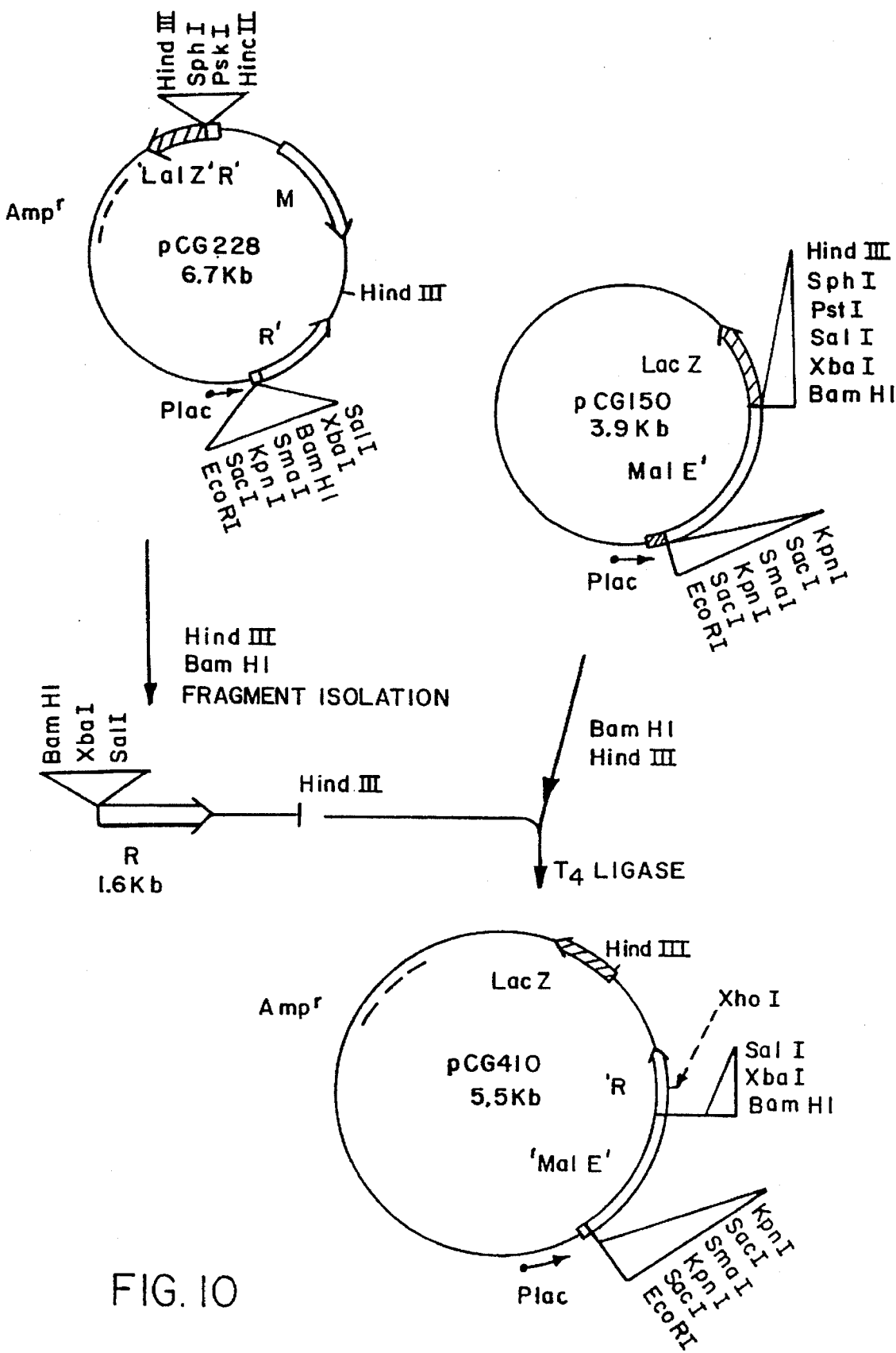

The outline of construction of plasmid pCG410 is illustrated in FIG. 9 and 10.

According to the published DNA sequence of Pst I restriction and modification system described in Walder et al., J. Biol. Chem Vol. 259 No. 12, pp. 8015–8026 (1984), the disclosure of which is hereby incorporated by reference, the restriction gene and the methylase gene are transcribed divergently from the promoter region between the two genes. There is a Hinc II restriction enzyme cleavage site at the eighth codon of the Pst I restriction gene. A Hind III DNA fragment (4.0 kb) containing Pst I restriction and modification genes has been cloned in the Bind III site of plasmid pBR322. This plasmid is pGW4400.

30 ug of plasmid pGW4400 DNA were cleaved with 30 units of Hind III restriction enzyme and 30 units of Pvu II restriction enzyme in 208 ul of Bind III digestion buffer followed by phenol/chloroform extraction and ethanol precipitation. The DNA was dissolved in 50 ul of TE buffer followed by mixing with 10 ul of loading buffer. A sample was elecrophoresed through 1% of low gelling temperature agarose. After electrophoresis the gel was stained with ethidium bromide and the DNA bands were visualized with UV irradiation as described in Example I. Three bands appeared on gel. The topmost one (4.0 kb) was cut out and the DNA was extracted from gel as described in Example I. The purified DNA fragment was ligated with 50 units of T4 DNA Ligase in 0.5 ml of ligation buffer followed by phenol/chloroform extraction and ethanol precipitation. The DNA was cleaved with 30 units of Hinc II restriction enzyme in 100 ul of Hinc digestion buffer followed by phenol/chloroform extraction and ethanol precipitation. The DNA was dissolved in 20 ul of DNA buffer.

5 ug of plasmid pUC18 DNA was cleaved with 10 units of Hinc II restriction enzyme followed by phenol/chloroform extraction and ethanol precipitation. The DNA was dissolved in 10 ul of DNA buffer.

Two DNA preparations, the 4.0 kb fragment from pGW4400 and the Hinc II cleaved pUC-18, were pooled, followed by adding 5 ul of 6× ligation buffer and 2 ul (or 10 units) of T4 ligase and incubated overnight at room temperature. The ligation solution was used to transform competent cells of JM 101 as described in Example I. The transformation mixture was plated on LB plates containing ampicillin 100 ug/ml, XG 20 ug/ml and IPTG 10-4M. After overnight incubation about 100 transformants were obtained. 20% of them were white. 32 white transformants were purified and DNA minipreparations were made from the white transformants as described in Example I. The recombinant plasmids were identified by restriction enzyme analysis. One recombinant plasmid was chosen as pCG228 whose construction is presented in FIG. 9.

10-20 ug of plasmid pCG228 DNA purified with BND cellulose were cleaved with 20 units of BamH I restriction enzyme and 20 units of Bind III restriction enzyme in 100 ul of the BamH I-Bind III double digestion buffer (10 mM Nacl, 3 mM dithiothrietol 10 mM MgCl2). The 1.6 kb BamHi-BindIII DNA fragment contained the Pst I restriction gene whose promoter and first 7 codohs had been replaced by a BamHi-XbaI-SalI polylinker. This fragment was purified from low gelling temperature agarose gel as described in Example I. The purified DNA fragment was dissolved in 10 ul of DNA buffer.

10 ug of plasmid pCG150 were cleaved with BamH I and Bind III restriction enzymes followed by phenol/chloroform extraction and ethanol precipitation as described above. The DNA was dissolved in 10 ul of DNA buffer.

The two DNA preparations, the 1.6 kb BamH I-Hind III fragment and pCG150 cleaved vector, were pooled and ligated with 10 units of T4 DNA Ligase in 30 ul of ligation buffer by incubation of the ligation solution overnight at 16° C. The ligation solution was used to transform competent cells of MC4100 habouring plasmid pACYC184 (Lac I),. pACYC184 (Lac I) (Chang, etal., J. Bact. Vol.134 No.3 pp.1141–1156 (1978), the disclosure of which is hereby incorporated by reference) is a multicopy plasmid and is compatible with plasmid pBR322 in *E. coli* K12. A DNA fragment containing the Lac I gene was inserted into the EcoR I cutting site of pACYC184. This is plasmid pACYC184 (Lac I). In order to prepare competent cells of MC4100 harbouring pACYC184 (Lac I), MC4100 was first transformed with plasmid pACYC184 (Lac I). The transformants (tetracycline resistant) were then used to prepare competent cells as described in Example I. These are competent cells of MC4100 barbouting pACYC184 (Lac I). The transformation mixture was placed onto LB plates containing ampictllin, 100 ug/ml, tetracycline 20 ug/ml. About 50–100 transformants appeared on each plate after overnight incubation. The plates were replicated onto LB plates containing ampicillin 100 ug/ml, tetracycline 20 ug/ml and IPTG $4 \times 10^{-4}$M. The replicated plates were incubated overnight at 37° C. The transformants which grew on LB-ampicillin-tetracycline plates but failed to grow on LB-amptcillin-tetracycline-IPTG plates were saved and purified on LB-amptcillin-tetracycline plates. DNA minipreparations were made from the IPTG sensitive transformants and used to transform JM103 or 71-18. The transformants which were resistant to ampicillin but sensitive to tetracycline and $10^{-5}$M IPTG were saved. DNA mini preparations were made from these IPTG sensitive transformants and analyzed with restriction enzyme digestions. One recombinant plasmid was chosen as pCG410 whose construction is presented in FIG. 10.

Affinity Chromatography of Pst I—Mal E Fusion

*E. coli* strain MC4100 harbouring both plasmids pCG410 and pACYC184 (Lac I) was cultivated to late log phas in rich medim containing ampicillin 100 ug/ml and tetracycline 20 ug/ml at 37° C. IPTG was added to $4 \times 10^{-4}$M and the culture was incubated for additonal 1.5 hours at 37° C. The cells were harvested and the cellular crude extract was prepared as described in Example I. The cellular extract was applied to a cross-linked amylose column and affinity chromatography was performed as described in Example I. More than 99% of (OD 280) absorbing material in the cellular crude extract passed through cross-linked amylose column. Less than 1% of OD 280 absorbing material bound to the column could be eluted with the maltose buffer. Pst I restriction enzymatic activity was found in the pass through fraction and in the maltose buffer eluted fractions. High levels of non-specific DNAase were found in the pass through fraction but not in the maltose buffer eluted fractions. The pass through fractions consisting of the main protein peak were pooled and applied onto another cross-linked amylose column. Neither protein nor DNAase acitivity, including Pst I restriction like activity, were found to be retained by the column. In contrast, when the Pst I restriction like enzymatic activity in the maltose eluted fractions was pooled, dialysed and reapplied onto another cross-linked amylose column, all of the activity was retained by column and could be eluted with maltose buffer.

Polyacrylamide Gel Electrophoresis

Figure 11:
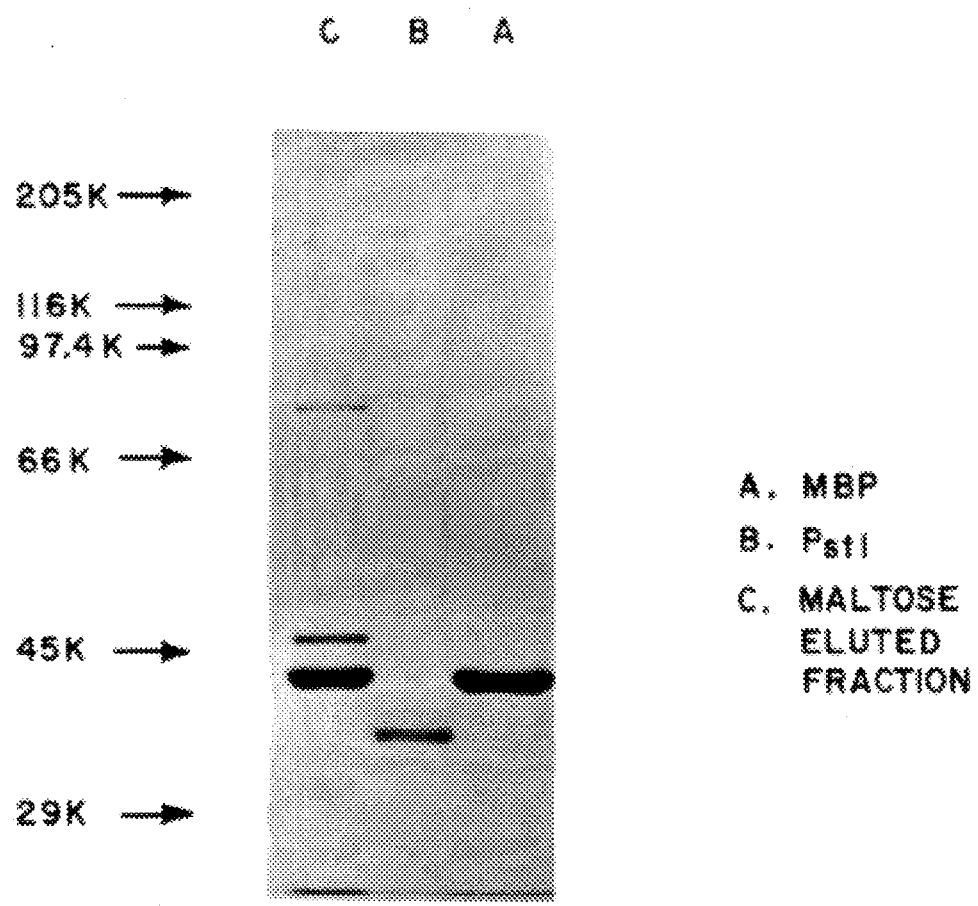
FIG. 11 illustrates the SDS polyacrilamide gel electrophorests of the product of the mal E—Pst I fusion.

The fractions consisting of the main protein peak and the maltose eluted peak were pooled seperately. The maltose eluted pool was concentrated 25–50 fold as described in Example I. The pooled samples above were used for SDS polyacrylamide gel electrophorests as described in Example I. The results are shown in FIG. 11. Three proteins were eluted with the maltose buffer as determined by the SDS gel. The topmost band represents a protein whose molecular weight is estimated at 78 K daltons corresponding to that deduced from the sequence of the MalE-PstI gene-fusion. The lowest band comigrated with native maltose binding protein and was believed to represent the product of the Mal E gene of the host cell. It Is also possible that this represents the degraded product from the hybrid polypeptide, formed as a protease resistant domain in the hybrid polypeptide. The third band which migrated slightly slower than either MBP or Pst I proteins maybe degradation products.

EXAMPLE III

Preparation of Immobilized Protein Bioreactor

Ten milliliters of late log phase culture of strain SF1362 harboring plasmid pCG325 was harvested by centrifugation. The cell pellet was suspended in 2 ml. of buffer (10 mM Tris-HCI pH 7.2). Crude extract was prepared as described in Example I. The cell extract was applied to a 0.6×2.5 cm cross-linked amylose column, and washed with buffer as in Example I.

Cleavage of ONPG by the Bioreactor

The bioreactor column was equilibrated with Z buffer as in Example I at room temperature. 500 ml of Z buffer containing 0.1% ONPG was applied to the column at room temperature with a flow rate of 0.5 ml/min. The pass through fraction was collected and the conversion to ONPG to ONP and free sugar was determined to be greater than 95%. After use the bioreactor may washed with Z buffer and stored at 4 degrees centigrade. The bioreactor can be reused multiple times.

EXAMPLE IV

Example IV describes the cloning, expression and purification of paramyosin as a product of the male paramyosin gene fusion.

Preparation of the binding protein fusion vector containing the Factor Xa protease recognition site Plasmid pCG806 is the source of the binding protein fusion vector containing the Factor Xa protease recognition site, which is prepared by insertion of DNA that codes for that site into pCG806. An additional four base pair insertion is then produced to shift the translational reading frame of the insert so that it corresponds to that of the male portion of pCG806. The plasmid produced is pCG806fx. The DNA insert that codes for the Factor Xa recognition site also contains a site for the restriction endonuclease StuI, which allows for the cloning of any DNA fragment immediately following the protease site. The construction of pCG806fx is illustrated in FIG. 12A.

2 μg each of the oligonucleotides 5'CATCGAGGGTAG-GCC 3' and 5'TACCCTCGATGGATC 3' were mixed in 45 μl of 50 mM Tris-HCl pH 7.4, 10mM MgCl$_2$, 2 mM dithiothreitol, and heated to 65° C. for 5 min. The mixture was cooled to 25° C., 2.5 μl 20 mM ATP and 5 μl T4 kinase (50 units) was added, and the mixture was incubated at 37° C. for 1 hr. The mixture was then cooled to 16° C., 5 μl T4 ligase (2000 units) was added, and the mixture was incubated for 12 h at 16° C. The mixture was then phenol and chloroform extracted and ethanol precipitated. The DNA was resuspended in 50 μl BamHI buffer and 5 μl (125 units) of BamHI was added and the mixture was incubated for 2 h at 37° C. The mixture was heated to 65° C. for 2 h to inactivate the restriction enzyme.

10 μg of pCG806 DNA in BamHI buffer was digested with 2 μl BamHI (40 units) for 1 h at 37° C. 0.1 unit of calf intestinal phosphatase was added and the mixture was incubated an additional 20 min at 37° C., then phenol and chloroform extracted and ethanol precipitated. This DNA was resuspended in 50 μl ligase buffer and pooled with 5 μl of the kinased, ligated and BamHI digested oligonucleotides described in the preceding paragraph. 1 μl T4 ligase (400 units) was added to the mixture and the mixture was incubated at 16° C. for 12 h and then used to transform SF1362 as described by Silhavy et al., supra. 50 plasmid DNA minipreparations from ampicillin resistant transformants were prepared as described by Silhavy et al., supra., and tested for the presence of a StuI restriction endonuclease site as follows. 10 μl of plasmid DNA (approximately 0.5 μg) was mixed with 10 μl of 200 mM NaCl, 20 mM Tris-HCl, 20 mM MgCl$_2$, 2 mM dithiothreitol containing 4 units of StuI restriction endonuclease and incubated for 2 h at 37° C., and the sample was analyzed by gel electrophoresis. A plasmid that had acquired a new StuI site was chosen. In order to ensure that only a single oligonucleotide (containing the StuI and Factor Xa sites) would be present, 1 μg of the plasmid that had acquired a StuI site was digested with StuI as described above, and the linear plasmid DNA was subjected to electrophoresis on a low gelling temperature agarose gel, the single DNA band cut out, purified and precipitated with ethanol as described in Example I. 50 μl of this DNA in agarose was melted at 65° C. for 10 min., cooled to 37° C., and 6 μl of 10× ligation buffer and 6 μl of T4 ligase was added and the mixture was incubated at room temperature for 12 h. The ligation mixture was then heated to 65° C. for 10 min., cooled to 37° C., and mixed with 200 μl of TB 1 cells made competent as described. After 2 min. at 37° C., aliquots were spread on LB plates containing 200 μg/ml ampicillin and incubated at 37° C. overnight. Plasmid DNA was prepared from one transformant by CsCl gradient centrifugation as described by Maniatis et al., supra. pp.86–95, and the DNA from the malE-lacZ joint region was sequenced to confirm the expected sequence. This plasmid was called pCG806F.

The malE portion of pCG806F and the region coding for the four amino acid Factor Xa recognition site are not in the same translational reading frame. A four base pair insertion was created that shifts these two elements into the same reading frame, and at the same time shifts the lacZ portion out of frame to the male portion. 2 μg pCG806F DNA in 20 μl XmaI buffer was digested with 5 units XmaI, phenol extracted and ethanol precipitated. The DNA was resuspended in 20 μl Klenow buffer (10 mM Tris-HCl pH7.5, 10 mMMgSO$_4$, 50 mM NaCl 1 mM dithiothreitol, 50 μM each dATP, dCTP, dGTP and dTTP) and 5 units DNA polymerase I, Klenow fragment was added. The mixture was incubated at room temperature for 30 min., phenol extracted and ethanol precipitated, then resuspended in 50 μl ligase buffer. 5 μl T4 ligase (2000 units) was added and the mixture was incubated at 16° C. 12 h. The ligation mixture was used to transform competent cells of E. coli strain 71-18 and plated on LB plates containing 200 μg/ml ampicillin and 20 μg/ml of the chromogenic β-galactosidase substrate 5-bromo-4-chloro-3-indolyl-β-D-galactoside (XGal.) After overnight incubation at 37° C., a white (Lac–) transformant was purified and DNA was prepared by equilibrium centrifugation in a CsCl gradient as described by Maniatis et al., supra. The expected DNA sequence was confirmed by the presence of a new EagI site created by filing in the XmaI site, and by DNA sequencing. This plasmid was named pCG806fx. The sequence of the Factor Xa recognition site coding region of pCG806fx is presented in FIG. 12A. A schematic diagram of pCG806fx is presented in FIG. 12B.

As described above, the lacZ$_\alpha$ region of pCG806fx is out of frame from the malE region. This precludes the use of a Lac+ to Lac– conversion as an indicator of cloning an insert into the StuI site. In order to restore this useful feature, a four base pair deletion was produced following the StuI site of pCG806fx. 2 μg pCG806fx DNA in 10 mM Tris-HCl pH7.5, 10 mM MgCl$_2$, 1 mM dithiothreitol, 100 mM NaCl, containing 4 units SphI was incubated at 37° C. for 2 h. This mixture was diluted with 20 µl 10 mM Tris-HCl pH7.5, 10 mM MgCl$_2$, 1 mM dithiothreitol, containing 100 µM (each) dATP, dCTP, dGTP and dCTP. 1 µl DNA polymerase I, Klenow fragment (5 units) was added and the reaction was incubated at room temperature for 1 h. 1 µl 100 mMATP and 2.5 µl T4 ligase (1000 units) was added, and the mixture was incubated an additional 12 h. This mixture was used to transform TB1 cells, and the cells were plated on LB plates containing 200 µg/ml ampicillin and 20 µg/ml XGal. After overnight incubation at 37° C., a blue (Lac+) colony was purified and used to prepare plasmid DNA by CsCl gradient centrifugation. The DNA of the joint region was sequenced to confirm the expected sequence. The plasmid produced in this procedure was named pCG807fx.

Construction of pCG806fx/para

The vector pCG806fx was used to construct a gene fusion between male and a portion of the paramyosin gene that was isolated from a library made by cloning cDNA fragments prepared from Dirofilaria immitis into λgt11. This construction was performed by isolating the EcoRI fragment coding for the paramyosin peptide and ligating it into the StuI site of pCG806fx.

100 mg of λcDi2, a λ phage containing a cDNA insert coding for most of the Dirofilaria immitis paramyosin gene was digested with 500 units of EcoRI in 200 µls of EcoRI buffer for 4 hours at 37° C. 40 µls of agarose gel loading buffer was then added to this solution and the sample was electrophoresed through a 1.0% agarose gel at 30 volts for 16 hours. A trough was then cut in front of the 2600 base pair paramyosin insert band and the insert band was electrophoresed at 100 volts for 1 hour onto a dialysis membrane placed in the trough. The DNA was washed off the membrane, phenol extracted, ethanol precipitated and redissolved in 100 µls of TE (10 mM Tris-HCl pH 8.0, 1 mM EDTA) and amount quantified by OD$_{260}$. 1 µg of the purified paramyosin DNA fragment was reacted with DNA Polymerase I, Klenow Fragment in 100 µls of DNA Polymerase I, Klenow Fragment buffer at room temperature for 30 minutes to make blunt the two ends of the DNA fragment. The reaction was stopped by incubation at 65° C. for 10 minutes. The DNA was then ethanol precipitated and redissolved in 20 µls of TE.

1 µg of pCG806fx was digested with 5 units of StuI in 20 µls of StuI buffer at 37° C. for 2 hours. The DNA was then phenol extracted, ethanol precipitated and redissolved in 20 µls of TE.

2 µls of StuI digested pCG806fx and all of blunt-end paramyosin DNA were pooled and ligated together in 50 µls of ligation buffer with 5 units of T4 DNA ligase at 4° C. for 16 hours. The reaction was stopped by incubation at 65° C. for 10 minutes. 20 units of StuI were added to the DNA and incubated at 37° C. for 2 hours. 25 µls of the ligated, StuI digested DNA was used to transform competent cells of *E. coli* strain 71-18. The transformation suspension was plated onto LB amp plates and incubated at 37° C. for 16 hours. 16 transformant colonies were picked from the LM amp plates and minipreparations of plasmid DNA prepared from each. The presence of paramyosin insert DNA was determined by digesting 5% of the plasmid DNA solution from each of the transformants with EcoRI in 20 µls of EcoRI buffer at 37° C. for 2 hours followed by electrophoresis through a 1.0% agarose gel at 100 volts for 2 hours. The paramyosin insert DNA has an asymmetric BgIII site, so that plasmids with the paramyosin insert DNA in the desired orientation yield a 1000 and a 5000 bp fragment when digested with BgIII. Plasmids with the paramyosin insert DNA in the opposite orientation yield two 3000 bp fragments when digested with BgIII. 5% of the DNA solution from each of the transformants that had been shown to have a 2600 bp insert were then digested with BgIII in BgIII buffer at 37° C. for 2 hours followed by electrophoresis through a 1.0% agarose gel at 100 volts for 2 hours. One transformant with the paramyosin insert DNA in the desired orientation was named pCG806fx-para. FIG. 12C shows the nucleotide sequence of the joint region between malE and the paramyosin coding sequence.

Purification and Factor Xa Cleavage of MBP-paramyosin

*E. coli* strain 71-18 bearing plasmid pCG806fx-para was grown and the MBP-paramyosin hybrid protein expressed and purified by affinity chromatography exactly as described for the MBP-β-galactosidase hybrid protein in Example I. Approximately 1 mg purified protein was obtained from each liter of culture grown. The protein solution eluted from the cross-linked amylose column was dialyzed against 4 changes of 1000 volumes 10 mM Tris-HCl pH 7.2 to remove maltose, and concentrated by filtration on an Amicon 8050 stirred cell to 0.6 mg/ml. An equal volume of glycerol was added to enhance stability upon storage at 20° C., giving a final concentration of 0.3 mg/ml.

The MBP-paramyosin hybrid protein was cleaved with Factor Xa as follows. 3ml of the hybrid protein solution was added to 3 ml of 10 mM Tris-HCl pH7.2 containing 50 µg of Bovine Factor Xa (C. M. Jackson et al., Biochemistry 7:4506, 1968) and incubated at room temperature for 6 h. The extent of cleavage was monitored by visualizing the disappearance of the hybrid protein and the appearance of its cleavage products after subjecting a sample of the reaction mixture to SDS-polyacrylamide gel electrophoresis.

After completion of the Factor Xa cleavage of the MBP-paramyosin hybrid protein, the MBP peptide was removed from the reaction mixture by repeating the cross-linked amylose affinity chromatography procedure. 0.7 ml 5M NaCl was added to the reaction mixture (final concentration 1M NaCl) and the mixture was loaded on a 3 ml column of cross-linked amylose equilibrated with 10 mM Tris-HCl 1M NaCl. This affinity chromatography step was repeated two additional times. The paramyosin produced by this procedure was free of greater than 95% of the MBP peptide as judged by SDS-polyacrylamide gel electrophoresis.

What is claimed is:

1. A method for producing and purifying a protein molecule comprising:
   a) constructing a DNA expression vector which expresses a hybrid polypeptide in a transformed host cell, the hybrid polypeptide comprising the protein molecule, a sugar binding protein or portion thereof having a specific affinity for a substrate which binds to the sugar binding protein, and a linking sequence interposed between said protein molecule and said sugar binding protein, or portion thereof, said linking sequence having a Factor Xa protease cleavage site;
   b) introducing the expression vector into an appropriate host cell and expressing the hybrid polypeptide;
   c) contacting the hybrid polypeptide produced by the transformed cell with the substrate to which the sugar binding protein binds;
   d) contacting the substrate bound hybrid polypeptide with a proteolytic agent that cleaves said linking sequence at the Factor Xa cleavage site, thus separating the protein molecule from the sugar binding protein; and
   e) recovering the target protein molecule.

2. The method of claim 1 wherein said proteolytic agent is Factor Xa protease.

3. A fusion vector for constructing an expression vector which expresses a sugar binding protein fused to a protein molecule to be purified, comprising:

(a) a DNA fragment coding for the sugar binding protein or portion thereof, having a specific affinity for a substrate which binds to the sugar binding protein; and (b) a DNA fragment which codes for a linking sequence having a Factor Xa protease cleavage site, wherein said DNA fragment is adapted for linking the DNA coding for the sugar binding protein with the DNA coding for the protein molecule.

4. A DNA expression vector for producing a purified protein molecule, which upon expression produces a sugar binding protein fused to the protein molecule, comprising:

(a) a first DNA fragment coding for the sugar binding protein or portion thereof having a specific affinity for a substrate which binds to the sugar binding protein; and (b) a second DNA fragment coding for the protein molecule to be purified; and (c) a linking DNA fragment coding for a linking sequence interposed between said first and second DNA fragments, wherein said linking sequence contains a Factor Xa protease cleavage site.

5. The expression vector of claim 4 wherein the linking DNA fragment comprises one or more restriction sites.

6. The expression vector of claim 5 wherein the linking DNA fragment comprises a StuI restriction site.

7. A method for producing and purifying a target protein molecule comprising:

a) constructing a DNA expression vector which expresses a hybrid polypeptide in a transformed host cell, the hybrid polypeptide comprising the target protein molecule and a sugar binding protein having a specific affinity for a substrate which binds to the sugar binding protein;

b) introducing the expression vector into an appropriate host cell and expressing the hybrid polypeptide;

c) contacting the hybrid polypeptide produced by the transformed cell with the substrate to which the sugar binding protein binds; and d) recovering the target protein molecule.

8. The method of claim 1 or 7, wherein the substrate is contained within an affinity column.

9. The method of claim 1 or 7, wherein the sugar binding protein is maltose binding protein.

10. The method of claim 1 or 7, wherein the substrate is selected from the group consisting of maltose, maltodextrins and macromolecular alpha (1→4) linked glucans.

11. The method of claim 1 or 7 comprising the further step of releasing the hybrid polypeptide from the substrate by contacting the bound hybrid polypeptide with a substance which displaces the hybrid polypeptide.

12. The method of claim 7, wherein the DNA coding for the hybrid polypeptide contains a linking DNA fragment which links the DNA encoding the protein molecule with the DNA encoding the binding protein.

13. A fusion vector for constructing an expression vector which expresses a sugar binding protein fused to a protein molecule to be purified, comprising:

(a) a DNA fragment coding for the sugar binding protein, the sugar binding protein having a specific affinity for a substrate which binds to the sugar binding protein; and (b) a DNA fragment which codes for a linking sequence for linking the DNA coding for the sugar binding protein with DNA coding for the protein molecule.

14. The fusion vector of claim 3 or 13, wherein the sugar binding protein is maltose binding protein.

15. The fusion vector of claim 3 or 13, wherein the linking sequence comprises one or more restriction sites.

16. The fusion vector of claim 13, wherein the linking sequence codes for a polypeptide which is recognized and cleaved by a proteolytic agent.

17. The fusion vector of claim 13, wherein the linking sequence codes for a spacer polypeptide which separates the binding protein from the protein molecule expressed by the expression vector.

18. The fusion vector of claim 13, comprising the plasmid pCG150.

19. A DNA expression vector for producing a purified target protein molecule, which upon expression produces sugar binding protein fused to the target protein molecule, comprising:

a) a DNA fragment coding for the sugar binding protein, the sugar binding protein having a specific affinity for a substrate which binds to the sugar binding protein; and b) a DNA fragment coding for the target protein molecule.

20. The expression vector of claim 4 or 19, wherein the sugar binding protein is maltose binding protein.

21. The expression vector of claim 4 or 19, wherein the linking sequence comprises one or more restriction sites.

22. The expression vector of claim 19, wherein a DNA fragment coding for a linking sequence is interposed between the DNA encoding the binding protein and the DNA encoding the protein molecule.

23. The expression vector of claim 19 wherein the linking sequence codes for a polypeptide which is recognized and cleaved by a proteolytic agent.

24. The expression vector of claim 19, wherein the linking sequence codes for a spacer polypeptide which separates the binding protein from the protein molecule expressed by the expression vector.

* * * * *

UNITED STATES PATENT AND TRADEMARK OFFICE
CERTIFICATE OF CORRECTION

PATENT NO.       : 5,643,758
APPLICATION NO.  : 08/374145
DATED            : July 1, 1997
INVENTOR(S)      : Guan et al.

It is certified that error appears in the above-identified patent and that said Letters Patent is hereby corrected as shown below:

Column 1, line 65, replace "fractionatton" with --fractionation--

Column 2, line 7, replace "electrophorests" with --electrophoresis--

Column 2, line 36, replace "universalire" with --universalize--

Column 3, line 19, replace "polypspride" with --polypeptide--

Column 3, line 41, replace "conventene" with --convenient--

Column 3, line 42, replace "polyltnker" with --polylinker--

Column 4, line 7, replace "polypepttde" with --polypeptide--

Column 4, line 14, replace "polypspride" with --polypeptide--

Column 4, lines 34-35, replace "electrophorests" with --electrophoresis--

Column 4, lines 40-41, replace "electrophorests" with --electrophoresis--

Column 5, line 45, replace "polypepttde" with --polypeptide--

Column 6, line 1, replace "arabthose" with --arabinose--

Column 6, line 8, replace "realrose" with --maltose--

Column 6, line 16, replace "1 um" with --1$\underline{u}$m --

Column 6, line 21, replace "BiophysicaI" with --Biophysical--

Column 6, line 56, replace "argtntne" with --arginine--

Column 7, line 28, replace "rictn" with --ricin--

Column 7, line 35, replace "occurtng" with --occuring--

Column 7, line 37, replace "amtno" with --amino--

Column 7, line 54, replace "polypsprides" with --polypeptides--

Column 8, line 13, replace "endonucteases" with --endonucleases--

UNITED STATES PATENT AND TRADEMARK OFFICE
CERTIFICATE OF CORRECTION

PATENT NO.        : 5,643,758
APPLICATION NO. : 08/374145
DATED             : July 1, 1997
INVENTOR(S)       : Guan et al.

It is certified that error appears in the above-identified patent and that said Letters Patent is hereby corrected as shown below:

Column 8, line 16, replace "cell is" with --cells--

Column 8, line 33, replace "termtnt" with --termini--

Column 8, line 65, replace "microrganisms" with --microorganisms--

Column 9, lines 19-20, replace "electrophorests" with --electrophoresis--

Column 10, line 38, replace "Mantatis" with --Maniatis--

Column 10, line 51, replace "dithigthreitol" with --dithiothreitol--

Column 11, line 3, replace "male" with --malE--

Column 11, line 31, replace "Yantsch" with --Yanisch--

Column 11, line 46, replace "Yantsch" with --Yanisch--

Column 11, line 51, replace "79∝99" with --79-99--

Column 11, line 61, replace "microlugs" with --microfuge--

Column 11, line 64, replace "electrephoresed" with --electrophoresed--

Column 12, line 6, replace "BindIII" with --HindIII--

Column 12, line 31, replace "Mind III" with --HindIII--

Column 12, line 52, replace "ug/mI" with --ug/ml--

Column 12, line 65, replace "restatted" with --restarted--

Column 13, line 5, replace "galactostdase" with --galactosidase--

Column 13, line 20, replace "ampictllin" with --ampicillin--

Column 13, line 45, replace "Ferenct" with --Ferenci--

Column 13, line 62, replace "galactostdase" with --galactosidase--

Column 14, line 2, replace "galactostdase" with --galactosidase--

UNITED STATES PATENT AND TRADEMARK OFFICE
CERTIFICATE OF CORRECTION

PATENT NO.         : 5,643,758
APPLICATION NO. : 08/374145
DATED                  : July 1, 1997
INVENTOR(S)       : Guan et al.

It is certified that error appears in the above-identified patent and that said Letters Patent is hereby corrected as shown below:

Column 14, line 13, replace "electrophorests" with --electrophoresis--

Column 14, line 19, replace "desrained" with --destained--

Column 14, line 19, replace "desraining" with --destaining--

Column 14, line 21, replace "electrophorests" with --electrophoresis--

Column 14, line 24, replace "polypspride" with --polypeptide--

Column 14, line 26, replace "math" with --main--

Column 14, line 31, replace "electrophorests" with --electrophoresis--

Column 14, line 32, replace "electrophorests" with --electrophoresis--

Column 14, line 33, replace "NAP0" with --NaPO--

Column 14, line 37, replace "polypspride" with --polypeptide--

Column 14, line 46, replace "galactostdase" with --galactosidase--

Column 14, line 49, replace "galactostdase" with --galactosidase--

Column 15, line 2, replace "Bind III" with --Hind III--

Column 15, line 6, replace "208 ul of Bind III" with --200 ul of Hind III--

Column 15, line 44, replace "Bind III" with --Hind III--

Column 15, line 45, replace "Bind III" with --Hind III--

Column 15, line 48, replace "codohs" with --codons--

Column 15, line 54, replace "Bind III" with --Hind III--

Column 15, line 63, replace "etal" with --et al--

Column 16, line 9, replace "ampictllin" with --ampicillin--

Column 16, line 16, replace "amptcillin" with --ampicillin--

UNITED STATES PATENT AND TRADEMARK OFFICE
CERTIFICATE OF CORRECTION

PATENT NO. : 5,643,758
APPLICATION NO. : 08/374145
DATED : July 1, 1997
INVENTOR(S) : Guan et al.

It is certified that error appears in the above-identified patent and that said Letters Patent is hereby corrected as shown below:

Column 16, line 17, replace "amptcillin" with --ampicillin--

Column 16, line 58, replace "electrophorests" with --electrophoresis--

Column 17, line 28, replace "male" with --malE--

Column 17, line 37, replace "male" with --malE--

Column 18, line 36, replace "male" with --malE--

Column 18, line 40, replace "mMMgSO$_4$" with --mM MgSO$_4$--

Column 19, line 5, replace "mMATP" with --mM ATP--

Column 19, line 17, replace "male" with --malE--

Signed and Sealed this

Twenty-fifth Day of September, 2007

JON W. DUDAS
*Director of the United States Patent and Trademark Office*